(12) United States Patent
Bean et al.

(10) Patent No.: US 7,594,906 B2
(45) Date of Patent: Sep. 29, 2009

(54) ABSORBENT ARTICLE HAVING A STRETCHABLE REINFORCEMENT MEMBER

(75) Inventors: Karen Hargett Bean, Cumming, GA (US); Sandra Marie Rogers, Appleton, WI (US); David L. Zenker, Neenah, WI (US); Dale Arthur Peterson, Saint Germain, WI (US); James Martin Kaun, Neenah, WI (US); Paul Windsor Estey, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1119 days.

(21) Appl. No.: 10/620,142

(22) Filed: Jul. 15, 2003

(65) Prior Publication Data
US 2005/0015068 A1 Jan. 20, 2005

(51) Int. Cl.
*A61F 13/15* (2006.01)
(52) U.S. Cl. .......................... 604/385.31; 604/385.101; 604/385.16; 604/385.21; 604/385.23
(58) Field of Classification Search ............ 604/385.31, 604/385.101, 385.01, 385.16, 385.21, 385.23
See application file for complete search history.

(56) References Cited

U.S. PATENT DOCUMENTS

| | | | |
|---|---|---|---|
| 2,161,539 A | 6/1939 | Swartz | |
| 2,964,039 A | 12/1960 | Johnson, Jr. et al. | |
| 3,085,309 A | 4/1963 | Olson | |
| 3,156,751 A | 11/1964 | Valdes et al. | |
| 3,587,579 A | 6/1971 | Sabee | |
| 3,629,047 A | 12/1971 | Davison | |
| 3,683,921 A | 8/1972 | Brooks et al. | |
| 3,768,479 A | 10/1973 | Widlund | |
| 3,816,231 A | 6/1974 | Marshall | |
| 3,856,012 A | 12/1974 | MacDonald et al. | |
| 3,862,877 A | 1/1975 | Camden | |
| 3,867,935 A | 2/1975 | Eisdorfer et al. | |

(Continued)

FOREIGN PATENT DOCUMENTS

AU 458424 2/1975

(Continued)

OTHER PUBLICATIONS

International Search Report for PCT/US2004/008428 dated Aug. 23, 2004, 4 pages.

(Continued)

*Primary Examiner*—Jacqueline F. Stephens
(74) *Attorney, Agent, or Firm*—Armstrong Teasdale, LLP

(57) ABSTRACT

An absorbent structure and method for making the absorbent structure including an absorbent core made from a matrix of fibers, wherein the matrix is reinforced with a stretchable reinforcing member, such as scrim. The absorbent matrix may be secured to the web of scrim with the scrim in a stretched condition. When the web of scrim is in an unstretched condition, the web of scrim partially gathers the absorbent core to form rugosities on the core. The reinforcing member can have a non-uniform transverse width to conform to the shape of the absorbent core. The absorbent structure can have multiple layers of reinforcing members. The reinforcing member has strands arranged in a pattern to facilitate stretching. A first set of strands can cross a second set of strands at junction in a non-orthogonal relationship.

40 Claims, 12 Drawing Sheets

U.S. PATENT DOCUMENTS

| | | |
|---|---|---|
| 3,888,248 A | 6/1975 | Moore et al. |
| 3,935,979 A | 2/1976 | Hickey |
| 4,001,472 A | 1/1977 | Thomas et al. |
| 4,028,455 A | 6/1977 | Ueda et al. |
| 4,141,772 A | 2/1979 | Buell |
| 4,217,078 A | 8/1980 | Buell |
| 4,235,237 A | 11/1980 | Mesek et al. |
| 4,300,562 A | 11/1981 | Pieniak |
| 4,303,189 A | 12/1981 | Wiley et al. |
| 4,392,862 A | 7/1983 | Marsan et al. |
| 4,425,127 A | 1/1984 | Suzuki et al. |
| 4,606,964 A | 8/1986 | Wideman |
| 4,639,253 A | 1/1987 | Dyer |
| 4,640,810 A | 2/1987 | Laursen et al. |
| 4,645,499 A | 2/1987 | Rupinskas |
| 4,666,647 A | 5/1987 | Enloe et al. |
| 4,674,966 A | 6/1987 | Johnson et al. |
| 4,704,112 A | 11/1987 | Suzuki et al. |
| 4,710,185 A | 12/1987 | Sneyd, Jr. et al. |
| 4,761,258 A | 8/1988 | Enloe |
| 4,764,325 A | 8/1988 | Angstadt |
| 4,765,780 A | 8/1988 | Angstadt |
| 4,773,903 A | 9/1988 | Weisman et al. |
| 4,775,579 A | 10/1988 | Hagy et al. |
| 4,810,568 A | 3/1989 | Buyofsky et al. |
| 4,834,735 A | 5/1989 | Alemany et al. |
| 4,837,715 A | 6/1989 | Ungpiyakul et al. |
| 4,904,440 A | 2/1990 | Angstadt |
| 4,908,175 A | 3/1990 | Angstadt |
| 4,915,897 A | 4/1990 | Farrington et al. |
| 4,915,993 A | 4/1990 | Ten Wolde |
| 4,927,346 A | 5/1990 | Kaiser et al. |
| 4,927,582 A | 5/1990 | Bryson |
| 5,004,579 A | 4/1991 | Wislinski et al. |
| 5,017,324 A | 5/1991 | Kaiser et al. |
| 5,124,188 A | 6/1992 | Roe et al. |
| 5,128,082 A | 7/1992 | Makoui |
| 5,139,841 A | 8/1992 | Makoui et al. |
| 5,144,729 A | 9/1992 | Austin et al. |
| 5,161,283 A | 11/1992 | Hansen |
| 5,219,633 A | 6/1993 | Sabee |
| 5,281,208 A | 1/1994 | Thompson et al. |
| 5,302,445 A | 4/1994 | DePetris et al. |
| 5,328,072 A | 7/1994 | Ruessmann et al. |
| 5,334,446 A | 8/1994 | Quantrille et al. |
| 5,389,095 A | 2/1995 | Suzuki et al. |
| 5,389,202 A | 2/1995 | Everhart et al. |
| 5,429,788 A | 7/1995 | Ribble et al. |
| 5,447,677 A | 9/1995 | Griffoul et al. |
| 5,466,409 A | 11/1995 | Partridge et al. |
| 5,486,167 A | 1/1996 | Dragoo et al. |
| 5,505,720 A | 4/1996 | Walters et al. |
| 5,514,120 A | 5/1996 | Johnston et al. |
| 5,527,300 A | 6/1996 | Sauer |
| 5,531,729 A | 7/1996 | Coles et al. |
| 5,536,264 A * | 7/1996 | Hsueh et al. ............... 604/368 |
| 5,591,148 A | 1/1997 | McFall et al. |
| 5,607,415 A | 3/1997 | Datta et al. |
| 5,614,283 A | 3/1997 | Potnis et al. |
| 5,622,581 A | 4/1997 | Ducker et al. |
| 5,672,306 A | 9/1997 | Sprang et al. |
| 5,704,931 A | 1/1998 | Holtman et al. |
| 5,756,039 A | 5/1998 | McFall et al. |
| 5,762,844 A | 6/1998 | Van Himbergen et al. |
| 5,772,813 A | 6/1998 | Bitowft et al. |
| 5,803,334 A | 9/1998 | Patel et al. |
| 5,818,719 A | 10/1998 | Brandon et al. |
| 5,871,613 A | 2/1999 | Bost et al. |
| 5,873,963 A | 2/1999 | Trombetta et al. |
| 5,902,757 A | 5/1999 | Stern et al. |
| 5,916,661 A | 6/1999 | Benson et al. |
| 5,925,439 A | 7/1999 | Haubach |
| 5,938,648 A | 8/1999 | LaVon et al. |
| 5,944,706 A | 8/1999 | Palumbo et al. |
| 5,947,945 A | 9/1999 | Cree et al. |
| 5,961,509 A | 10/1999 | Kling |
| 5,997,520 A | 12/1999 | Ahr et al. |
| 6,048,489 A | 4/2000 | Reiter et al. |
| 6,060,637 A | 5/2000 | Bitowft et al. |
| 6,090,994 A | 7/2000 | Chen |
| 6,107,538 A | 8/2000 | Young et al. |
| 6,203,654 B1 | 3/2001 | McFall et al. |
| 6,204,207 B1 | 3/2001 | Cederblad et al. |
| 6,258,996 B1 | 7/2001 | Goldman |
| 6,262,331 B1 | 7/2001 | Nakahata et al. |
| 6,284,943 B1 | 9/2001 | Osborn, III et al. |
| 6,296,862 B1 | 10/2001 | Paul et al. |
| 6,330,735 B1 | 12/2001 | Hahn et al. |
| 6,375,644 B2 | 4/2002 | Mizutani |
| 6,416,697 B1 | 7/2002 | Venturino et al. |
| 6,492,574 B1 | 12/2002 | Chen et al. |
| 6,533,978 B1 | 3/2003 | Wisneski et al. |
| 6,533,989 B1 | 3/2003 | Wisneski et al. |
| 6,575,948 B1 | 6/2003 | Kashiwagi et al. |
| 6,630,096 B2 | 10/2003 | Venturino et al. |
| 2001/0027305 A1 * | 10/2001 | Raidel et al. .......... 604/385.101 |
| 2001/0039405 A1 | 11/2001 | Keuhn, Jr. et al. |
| 2003/0116888 A1 | 6/2003 | Rymer et al. |
| 2003/0119401 A1 | 6/2003 | Chakravarty et al. |
| 2003/0132556 A1 | 7/2003 | Venturio et al. |
| 2003/0139721 A1 | 7/2003 | Melius et al. |
| 2003/0171728 A1 | 9/2003 | Heyn et al. |
| 2004/0061263 A1 | 4/2004 | Daniels et al. |
| 2004/0061264 A1 | 4/2004 | Heyn et al. |
| 2004/0092898 A1 | 5/2004 | Schafer et al. |
| 2004/0098838 A1 | 5/2004 | Venturino et al. |
| 2004/0102751 A1 | 5/2004 | Schueler, Jr. |
| 2004/0102752 A1 | 5/2004 | Chen et al. |

FOREIGN PATENT DOCUMENTS

| | | |
|---|---|---|
| DE | 198 23 954 A1 | 12/1999 |
| EP | 0 151 018 A2 | 8/1985 |
| EP | 0 226 939 A2 | 7/1987 |
| EP | 0 298 348 A1 | 1/1989 |
| EP | 0 399 511 A2 | 11/1990 |
| EP | 0 467 409 A1 | 1/1992 |
| EP | 0 297 180 B1 | 3/1992 |
| GB | 2 168 612 A | 6/1986 |
| JP | 09122172 | 5/1997 |
| JP | 10211236 | 8/1998 |
| WO | WO 93/18729 A1 | 9/1993 |
| WO | WO 96/00550 A1 | 1/1996 |
| WO | WO 98/22064 A1 | 5/1998 |
| WO | WO 99/22685 A1 | 5/1999 |
| WO | WO 99/25281 A1 | 5/1999 |
| WO | WO 00/10498 A1 | 3/2000 |
| WO | WO 00/37000 A1 | 6/2000 |
| WO | WO 00/37725 A1 | 6/2000 |
| WO | WO 00/56257 A1 | 9/2000 |
| WO | WO 00/63479 A1 | 10/2000 |
| WO | WO 01/92003 A1 | 12/2001 |
| WO | WO 03/059232 A2 | 7/2003 |

OTHER PUBLICATIONS

International Search Report for PCT/US2004/006915 dated Nov. 5, 2004, 7 pages.
International Search Report for PCT/US03/15959 dated Feb. 3, 2004.
International Search Report for PCT/US03/16480 dated Oct. 13, 2003.
International Search Report for PCT/US 03/01337 dated Jul. 21, 2003.
International Search Report for PCT/US 03/00293 dated Jul. 29, 2003.

* cited by examiner

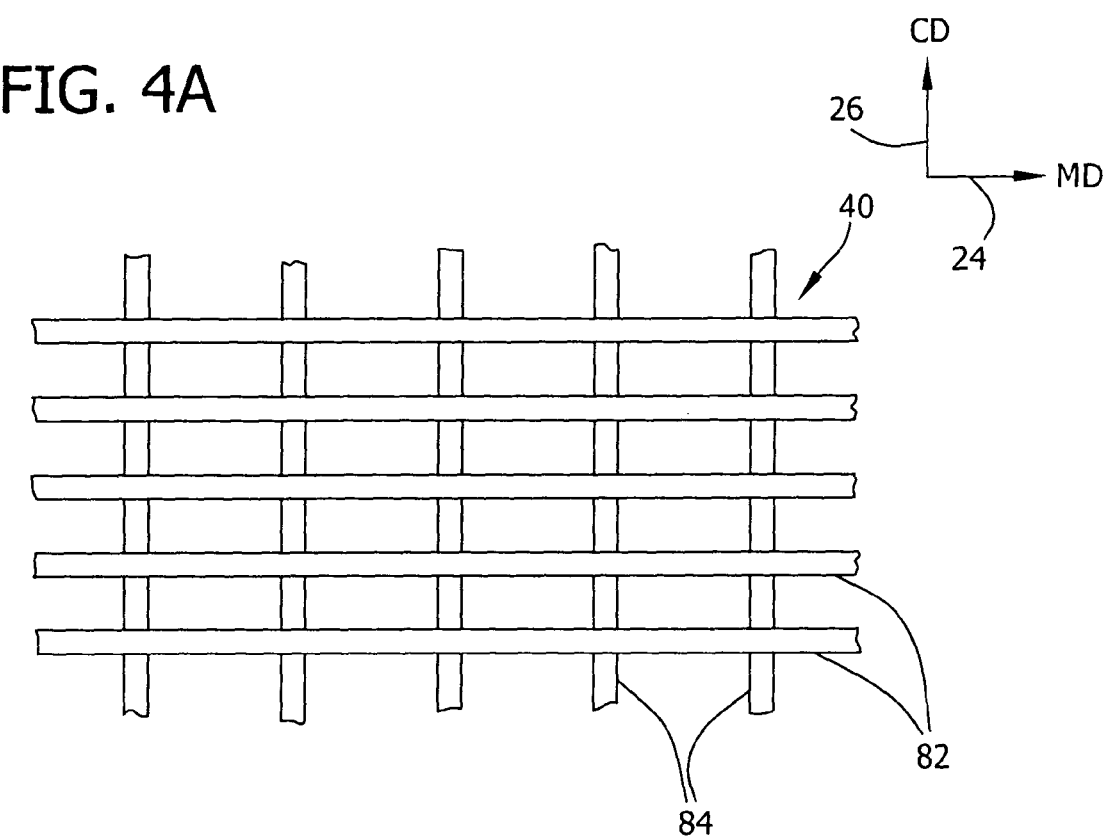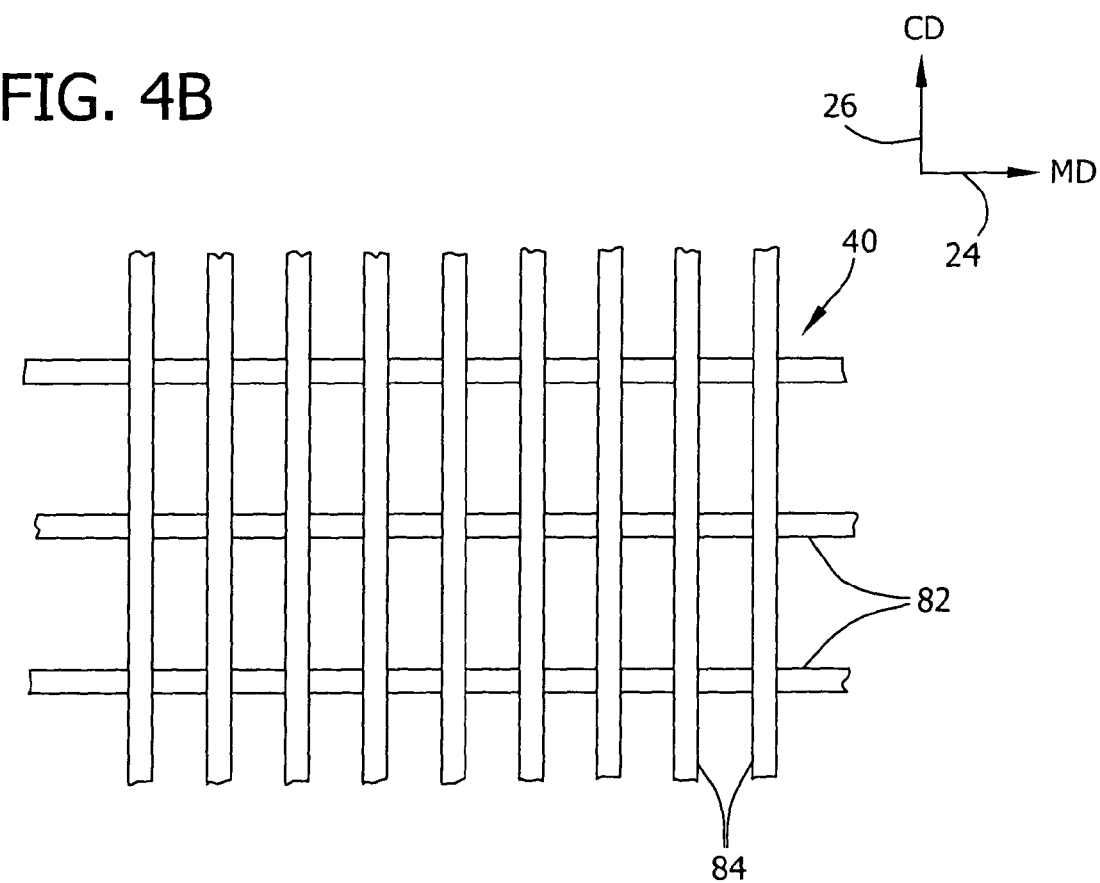

ABSORBENT ARTICLE HAVING A STRETCHABLE REINFORCEMENT MEMBER

BACKGROUND OF THE INVENTION

This invention relates generally to an absorbent article, and more particularly to improvements in scrim reinforced absorbent cores having reduced stiffness. The reinforced absorbent structure can be employed in absorbent articles, such as disposable diapers, children's training pants, feminine care articles, incontinence articles, bandages, and the like.

Absorbent articles typically include fluid absorbent structures or cores conventionally formed by air forming or air laying techniques, and are covered by an intake function liner and a barrier function liner. The manufacture of the absorbent core may begin by fiberizing a fibrous sheet of cellulose or other suitable absorbent material in a conventional fiberizer, or other shredding device, to form discrete fibers, and particles of superabsorbent material may be mixed with the discrete fibers. The fibers and superabsorbent particles are then entrained in an air stream and directed to and deposited on a foraminous forming surface to form an absorbent fibrous web. In addition, bonding agents or other strengthening components may be incorporated to provide a more stabilized web.

Other techniques have also been employed to form webs of stabilized absorbent material. Such techniques have included dry-forming techniques, foam-forming techniques, and various wet-laying and wet-forming techniques. The resulting webs of absorbent material have included fibers, natural fibers, synthetic fibers, superabsorbent materials, binders, and strengthening components in desired combinations. However formed, the absorbent web is then processed (e.g., cut into individual absorbent cores) and assembled with other components (intake and barrier layers) to produce a final absorbent article. Absorbent material webs have also been strengthened by adding reinforcing members on at least one side of the absorbent material webs. Such reinforcing members have included reinforcement filaments, tissue layers, fabric layers and netting materials. It is also known to add staple binder fibers to the absorbent materials upon formation of the absorbent material web. The binder fibers are activated by heat to produce adhesion of the absorbent materials.

Integrity of an absorbent core formed from such an absorbent material web is desirable to avoid bunching, clumping, cracking and separating of the absorbent core in either a wet or a dry state so as to improve the fit and comfort to the wearer of the absorbent article. Sagging and drooping of the absorbent article due to fluid insults can cause gaps between the article and the wearer's body which may lead to leaking. Poor integrity of the absorbent core results in absorbent cracking and separating in use which continues to be a common problem with conventional air-formed absorbent cores. The incorporation of a scrim reinforcement material internally into the structure of the absorbent core dramatically reduces this integrity problem. However, in some cases scrim reinforcement can also result in undesirable absorbent stiffness which adversely impacts conformability, fit and comfort, especially in the crotch region of the absorbent article. This is particularly relevant for a narrow crotch geometry, where the buckling span is shorter as compared to wide crotch executions.

As absorbent cores are made both thinner and narrower to achieve increased comfort (particularly in the crotch region), web stresses encountered in manufacture and use can be high, requiring better reinforcement. For instance in manufacture, tension on the absorbent core can be particularly high during start-up and shutdown of processing machinery, during removal from the forming surface, and during conveyance through component attachment and packaging machinery. In use, the lack of integrity can make the absorbent article fit poorly and impair product performance by breaking up the absorbent core, and thereby inhibiting fluid control, liquid handling and wicking which can contribute to leaking.

It is known to use a netting or scrim within the absorbent core which is connected to the fibrous absorbent material to hold the material together under loads. Conventional reinforcement scrims have exhibited shortcomings when employed to form desired absorbent structures and have not provided the desirable combinations of low cost, high strength and low irritation in addition to the basic attributes of comfort and high fluid absorption. For example, conventional reinforcement materials and formats have been relatively unstretchable and/or inflexible. Thus, an absorbent garment incorporating scrim may not readily conform to the wearer's body or give as the wearer moves or the absorbent core is loaded. As a result, it has been difficult to achieve an absorbent structure with desired stretchability and resistance to tears when exposed to the forces of movement and body exudates. Additionally, reinforcement scrims with widths suitable for the narrow crotch portion of the absorbent article have been used in the much wider waist portions of the article. As a result, it has been difficult to achieve an absorbent structure having the desired strength in the waist portions.

SUMMARY OF THE INVENTION

One embodiment of the invention is a stretchable absorbent structure for absorbing liquid. The absorbent structure has an absorbent member at least partially made of fibers having first, second and third regions. A first stretchable reinforcing member is located between the first region and the second region. A second stretchable reinforcing member is located between the second region and the third region. The first and second stretchable reinforcing members reinforce the absorbent member to maintain the structural integrity of the absorbent member under loads experienced by the absorbent structure.

Another embodiment of the invention is directed to a stretchable absorbent structure for absorbing liquid. The absorbent structure includes an absorbent member at least partially made of fibers and a reinforcing member at least partially embedded in the absorbing member for maintaining the structural integrity of the absorbent member. The absorbent member has a first axis extending generally lengthwise of the absorbent member and a second axis perpendicular to the first axis extending generally widthwise of the absorbent member. The reinforcing member includes a first set of substantially parallel strands, and a second set of strands that cross said first set of strands at junctions in a non-orthogonal relationship to define openings in the reinforcing member.

Another embodiment of the invention is directed to an absorbent structure for absorbing liquid. The absorbent structure includes an absorbent member at least partially made of fibers and a reinforcing member at least partially embedded in the absorbent member for maintaining the structural integrity of the absorbent member. The reinforcing member is connected to the absorbent member and at least partially gathers the absorbent member to form rugosities on the surface of the absorbent member.

Another embodiment of the invention is directed to a process for forming an absorbent core. The process includes holding an elastomeric reinforcing member in a stretched configuration and depositing absorbent material on the reinforcing member in the stretched configuration to form an absorbent member. The process further includes releasing the reinforcing member from the stretched configuration so that the absorbent member is at least partially gathered.

Another embodiment of the invention is directed to an absorbent structure for absorbing liquid. The absorbent structure includes an absorbent member at least partially made of fibers and a reinforcing member at least partially embedded in the absorbent member. The reinforcing member has a non-uniform transverse width and maintains the structural integrity of the absorbent member.

Another embodiment of the invention is directed to a process for forming absorbent cores. The process includes stretching a first portion of a reinforcing member so that said stretched portion has a transverse width wider than a second portion of said reinforcing member. The process further includes depositing absorbent material on the reinforcing member to form a first region of said absorbent material embedding the first portion of the reinforcing member therein and a second region of said absorbent material embedding the second portion, the first portion being wider than the second portion.

Other features, objects and advantages of the invention will become more apparent hereinafter.

BRIEF DESCRIPTION OF THE DRAWINGS

FIG. 4A is an enlarged, fragmentary plan view of a first reinforcement member shown elongated in the machine direction;

FIG. 4B is an enlarged, fragmentary plan view of a reinforcement member similar to 4A shown elongated in the cross direction;

Corresponding reference characters indicate corresponding parts throughout the several views of the drawings.

DETAILED DESCRIPTION OF THE DRAWINGS

The disclosure of co-assigned and co-pending patent application Ser. No. 10/306,086 for ABSORBENT ARTICLE WITH REINFORCED ABSORBENT STRUCTURE and patent application Ser. No. 10/306,185 for ABSORBENT ARTICLE HAVING DISCONTINUOUS ABSORBENT CORE, both filed Nov. 27, 2002, are incorporated herein by reference for the purpose of showing the various absorbent article constructions and materials that may be associated in certain executions of absorbent articles.

The technology of the invention can be configured to produce various types of desired absorbent articles. Such articles can include, for example, infant diapers, children's training pants, feminine care articles, adult incontinence garments, tissues, bandages and the like for use in absorbing various body exudates. The articles may be, but are not necessarily, disposable, and intended for limited use.

Figure 1:
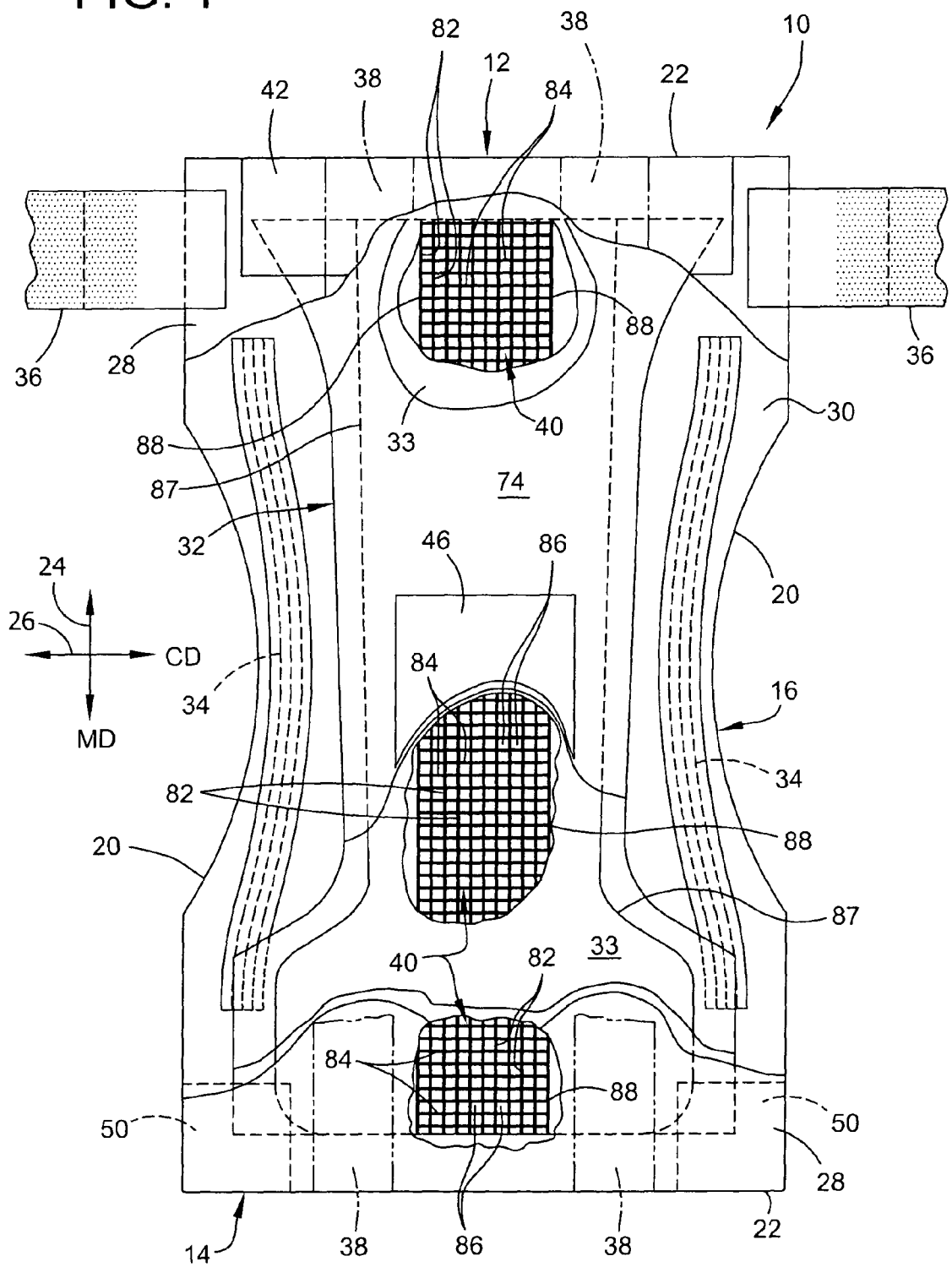
FIG. 1 is a top plan view of a representative absorbent article, partly broken away to show internal construction.

Referring now to the drawings, and in particular to FIG. 1, for disclosure purposes an absorbent article constructed according to the principles of the present invention is shown in the form of a diaper 10, broadly an absorbent article, unfolded and laid flat with substantially all elastic induced gathering and contraction areas removed. The illustrated diaper 10 has a first or back waistband portion 12, a second or front waistband portion 14 and an intermediate or crotch portion 16 that interconnects the back and front waistband portions. The diaper 10 extends lengthwise in a longitudinal or machine-direction 24, widthwise in a transverse or cross-direction 26, and has a depth or thickness in a thickness direction 25. For purposes of the present disclosure, the machine-direction 24 (called "MD") lies parallel to the plane of the diaper 10, and extends generally between the waistband portions 12, 14 of the diaper. The cross-direction 26 (called "CD") also lies parallel to the plane of the article, and is generally transversely oriented or perpendicular relative to the longitudinal MD strand direction 24. The thickness direction 25 (called "TD") is oriented substantially perpendicular or normal to the plane of both the elongate MD direction 24 and the transverse CD direction 26, and extends through the thickness of the diaper 10. In FIG. 1, the bodyside surface of the diaper which contacts the wearer faces upwardly and portions of the structure are partially cut away to more clearly show the interior construction of the diaper 10. The outer edges of the diaper define a periphery with longitudinally extending side edges 20 and transversely extending end edges 22. The side edges 20 will define leg openings for the diaper 10, in use.

With regard to the designated surfaces of the article, the various inward or bodyside surfaces are configured to face against the body of the wearer when the article is placed in use. The designated outward surfaces of the article are configured to face away from the wearer's body when the article is placed in use. The diaper 10 may have any desired shape, such as rectangular, I-shaped, a generally hourglass shape, or a T-shape.

The diaper 10 includes an absorbent inner structure, generally indicated at 32, having an absorbent core 33 (broadly, "an absorbent member") which may include both absorbent fibers and superabsorbent material (SAM) to be described.

Figure 2:
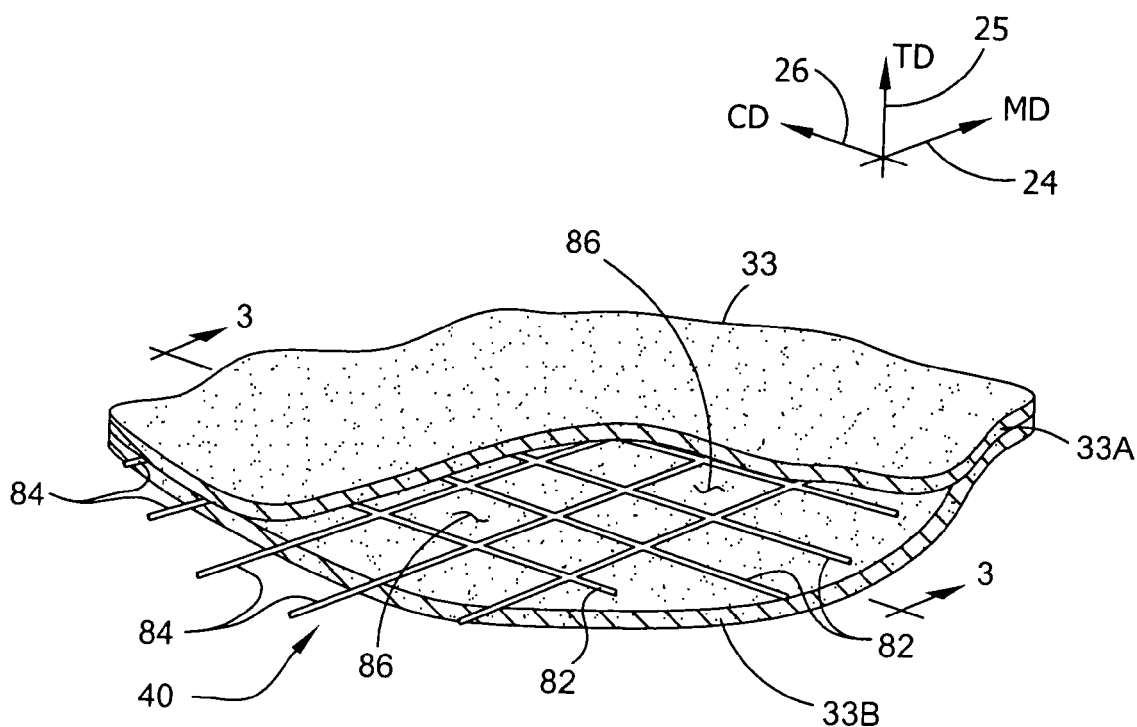
FIG. 2 is an enlarged, fragmentary perspective view of a typical absorbent core, partially broken away to show internal placement of a reinforcement member.

The absorbent core 33 may also include other fibers which are not absorbent. A web of scrim 40 (broadly, "a reinforcing member") is suitably located roughly in the middle of the absorbent core 33 (FIG. 2) for reinforcing the fibrous absorbent core to enhance the integrity of the core during use as will be described more fully hereinafter. The actual TD direction orientation of the web of scrim 40 between major surfaces of the absorbent core 33 may vary in applications where the core has a non-constant thickness. It is also to be understood that the web of scrim can be placed away from the middle, toward one side surface within the absorbent core and still come within the scope of the invention. A backsheet barrier layer 30 and a liquid permeable topsheet layer 28 are arranged on opposite sides from each other and the absorbent inner structure 32 is located between these layers. Typically, the backsheet barrier layer 30 is liquid impermeable, but may be liquid permeable for some applications without departing from the scope of the present invention. In use, the diaper 10 is fitted onto the lower torso and around the upper legs of a wearer (e.g., a child or infant), assuming a curved and three dimensional configuration in which parts of the back and front waistbands portions 12, 14 are overlapped or lie in close proximity to each other.

It will be understood that different absorbent articles to which the invention applies may require different features or combinations and arrangements of parts. The absorbent article selected for disclosure is a child's diaper 10, and a brief discussion of certain diaper features is believed to be relevant including diaper fastening systems and elastomeric gathering members, as now described.

A diaper fastening system includes a first fastener component in the form of fastener tabs 36 on one waist band portion 12 and a second fastener component in the form of landing zone patches 50 on the other waistband portion 14 to hold the article in place on a wearer so that the back portion overlaps the front portion. The landing zone patches 50 provide a target area for releasable and re-attachable securement with the fastener tabs 36. The landing zone patches 50 are positioned on the outward surface of the backsheet barrier layer 30. It is understood that an alternate fastening arrangement (not shown) could be used in which a front waistband portion overlaps the back waistband portion, whereby the front waistband portion would be the "first" waistband portion and the back waistband region would be the "second" waistband portion. One or more alternative fastener tabs and landing patch members can be selectively placed on the first or second waistband portions. The landing zone patches 50 and the fastener tabs 36 can be made of a substantially non-elastomeric material, such as polymer films or tapes, woven or non-woven fabrics, or the like. The landing zone patch 50 and the fastener tabs 36 could also be made of a substantially elastomeric material, such as a stretch-bonded-laminate (SBL) material, an elastomeric neck-bonded-laminate (NBL) material, an elastomeric film, an elastomeric foam material, or the like which is elastomerically stretchable.

In a broad context, the aforesaid fastening mechanism between the selected first and second fastener components may be adhesive, cohesive, mechanical or combinations thereof. Desirably, the first and second fastener components include complementary elements of cooperatively interengaging mechanical-type fasteners such as hooks, buckles, snaps, buttons and the like. As shown, the preferred mechanical fastening system is of the hook-and-loop type. Such fastening systems typically include a first attachment member in the form of a "hook" or hook-like, male component, and a second member in the form of a cooperating "loop" or loop-like, female component that is engaged and releasably interconnected with the first hook component. Such conventional systems are, for example, available under the VELCRO trademark, and the hook element may have a single-prong hook configuration, a multiple-prong hook configuration or a generally continuous, expanded-head configuration, such as provided by a mushroom-head type of hook element. The loop element may be a woven, nonwoven or knitted fabric, or a perforated or apertured layer, as well as combinations thereof.

The diaper typically also has a system of elastomeric gathering members, including leg elastics 34 to hold the diaper 10 closely around the legs and a waist elastic 42 (located in the back waistband portion 12) to draw the diaper around the waist. In addition, elasticized containment flaps 38 (shown in phantom) may be provided to extend generally lengthwise in the machine-direction 24 of the diaper 10. The containment flaps 38 are typically positioned laterally inboard from the leg elastics 34, and substantially symmetrically placed on each side of the longitudinal centerline of the diaper to closely contact and conform to the contours of the wearer's body. Examples of suitable containment flap constructions are described in U.S. Pat. No. 4,704,116 entitled DIAPERS WITH ELASTICIZED SIDE POCKETS issued Nov. 3, 1987, and U.S. Pat. No. 5,562,650 entitled ABSORBENT ARTICLE HAVING AN IMPROVED SURGE MANAGEMENT issued Feb. 13, 1996. Alternative configurations may include internal, elasticized, containment waist flaps, such as those described in U.S. Pat. No. 4,753,646 entitled DIAPER WITH WAIST FLAPS issued Jun. 28, 1988; and in U.S. Pat. No. 5,904,675 entitled AN ABSORBENT ARTICLE WITH IMPROVED ELASTIC MARGINS AND CONTAINMENT SYSTEM issued May 18, 1999. Such containment waist flaps (not shown herein) may be composed of a wettable or non-wettable material, as desired, and the waist flap material may be substantially liquid-impermeable, permeable to only gas, or permeable to both gas and liquid.

The diaper 10 also includes a surge management member 46 which helps to control surges or gushes of liquid that may be rapidly introduced into the absorbent structure of the article. Desirably, the surge management member 46 can rapidly accept and temporarily hold the liquid prior to releasing or wicking the liquid into the main absorbent inner structure 32. In the illustrated FIG. 1 embodiment, for example, the surge management member 46 is located on an interiorly facing side of the topsheet layer 28 so as to be interposed between the topsheet layer 28 and the absorbent core 33. Examples of suitable surge management members 46 are described in U.S. Pat. No. 5,486,166 issued Jan. 23, 1996 entitled FIBROUS NONWOVEN WEB SURGE LAYER FOR PERSONAL CARE ABSORBENT ARTICLES AND THE LIKE; and U.S. Pat. No. 5,490,846 issued Feb. 13, 1996 entitled IMPROVED SURGE MANAGEMENT FIBROUS NONWOVEN WEB FOR PERSONAL CARE ABSORBENT ARTICLES AND THE LIKE.

As indicated, the backsheet barrier layer 30 is located along an outside surface of the absorbent inner structure 32 (away from the wearer) and desirably comprises a substantially liquid impermeable material, such as a thin plastic film, or other relatively soft and flexible material. As used herein, the term "flexible" refers to materials which are compliant and which will readily conform to the general shape and contours of the wearer's body. The primary function of the backsheet barrier layer 30 is to contain or hold the exudates absorbed into the absorbent inner structure 32 and prevent the soiling of outside articles which contact the diaper 10, such as bed sheets and overgarments. In a particular embodiment of the invention, the backsheet barrier layer 30 can include a film, such as a polyethylene film, having a thickness of from about 0.012 millimeters (0.5 mil) to about 0.051 millimeters (2.0 mil). For example, the backsheet film can have a thickness of about 0.032 millimeters (1.25 mil). Alternative constructions of the backsheet barrier layer 30 may comprise a woven or non-woven fibrous web that is totally or partially constructed or treated to impart the desired levels of liquid impermeability to selected regions that are adjacent or proximate the absorbent inner structure. Specific examples of acceptable alternate backsheet or barrier materials are disclosed in co-assigned patent application Ser. No. 10/306,086 (previously cited and herein incorporated by reference).

As also indicated, the topsheet layer 28 presents a body-facing surface that is compliant, soft-feeling, and non-irritating to the wearer's skin. Further, the material of the topsheet layer 28 is more hydrophobic than the absorbent core 33, but is sufficiently porous to be liquid permeable, thus permitting fluids to readily pass through its surface ply thickness to reach the absorbent core structure 33. A suitable topsheet layer 28 may be manufactured from a wide selection of materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in the absorbent core 33. Specific examples of acceptable alternate topsheet layer materials are disclosed in co-assigned patent application Ser. No. 10/306,086 (previously cited and incorporated herein by reference).

The absorbent inner structure 32 has a construction that is generally compressible, conformable, non-irritating to the wearer's skin, and capable of absorbing and retaining body exudates. It should be understood that, for purposes of this invention, the absorbent inner structure 32 comprises several parts that are assembled together. The absorbent core 33 of the absorbent inner structure 32 may be constructed of any of a number of absorbent materials, as are well known in the art. For example, the absorbent core 33 may be provided by a layer of coform, meltblown fibers, bonded carded webs, a wetlaid body, tissue laminates, foams, a surge/air formed composite and the like or combinations thereof. In particular, the absorbent core 33 may be provided as a combination of hydrophilic fibers, and high-absorbency material.

The absorbent core 33 may also be zoned to provide for additional retention of liquid (as compared to the other regions of the core 33). Descriptions of ways to form zoned absorbent cores are disclosed in co-assigned U.S. Pat. No. 4,761,258 entitled CONTROLLED FORMATION OF LIGHT AND HEAVY FLUFF ZONES issued Aug. 2, 1988; U.S. Pat. No. 6,330,735, entitled APPARATUS AND PROCESS FOR FORMING A LAID FIBROUS WEB WITH ENHANCED BASIS WEIGHT CAPABILITY issued Dec. 18, 2001; and U.S. patent application Ser. No. 10/207,929 entitled APPARATUS AND FORM FOR MAKING AN AIR FORMED FIBROUS WEB filed Jul. 30, 2002.

Various types of wettable, hydrophilic fibrous material can be used to provide the fiber material for the absorbent core 33. Examples of suitable fibers include naturally occurring organic fibers composed of intrinsically wettable material, such as cellulose fibers including wood pulp fibers which can be curled, crosslinked or otherwise mechanically or chemically modified. Other examples of suitable fibers include synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with another material that has a suitable hydrophilic moiety and is not readily removable from the fiber, or by sheathing the nonwettable, hydrophobic fiber with a hydrophilic polymer during or after the formation of the fiber.

The high-absorbency or super absorbent material (SAM) used in the absorbent core 33 may comprise absorbent gelling materials, such as superabsorbent materials. Absorbent gelling materials can be natural, biodegradable, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces. Examples of synthetic absorbent gelling material polymers include the acidic or alkali metal and ammonium salts of poly(acrylic acid) and poly (methacrylic acid), poly(acrylamides), poly (vinyl ethers), maleic anhydride copolymers with vinyl ethers and alpha-olefins, poly(vinyl pyrrolidone), poly(vinylmorpholinone), poly(vinyl alcohol), or basic or chloride and hydroxide salts of polyvinyl amine, polyamine polyquarternary ammonium, polyimine, hydrolyzed polyamide, and mixtures and copolymers thereof. Further polymers suitable for use in the absorbent core include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed in U.S. Pat. No. 3,901,236 issued Aug. 26, 1975 and processes for preparing synthetic absorbent gelling polymers are disclosed in U.S. Pat. No. 4,076,663 issued Feb. 28, 1978 and U.S. Pat. No. 4,286,082 issued Aug. 25, 1981. Superabsorbent materials are well known in the art, and are readily available from various suppliers. For example, FAVOR SXM 880 superabsorbent is available from Stockhausen, Inc., a business having offices located in Greensboro, N.C., U.S.A.; and DRYTECH 2035 is available from Dow Chemical Company, a business having offices located in Midland, Mich., U.S.A.

The high-absorbency material used in the absorbent core 33 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent core 33. Desired for use are particles having an average size of from about 20 micrometers to about 1 millimeter. "Particle size" as used herein means the weighted average of the smallest dimension of the individual particles. The high-absorbency material can be separated or in-situ polymerization formed on the fiber and still within the scope of this invention.

The absorbent materials and superabsorbent materials may be integrated into the absorbent core by any of several known methods such as a dry-forming technique, an air forming technique, a wet-forming technique, a foam-forming technique, in-situ polymerization technique or the like.

In desired arrangements of absorbent articles, still other features may be employed to improve the strength, integrity, absorbency and comfort of the article. For instance, to improve the containment of the high-absorbency material, the absorbent inner structure 32 can include a barrier layer 74, which is placed immediately adjacent to the absorbent core 33 and may be bonded to the absorbent core and to the various other components of the diaper 10. In one embodiment, the barrier layer 74 is a wrap sheet that encloses substantially all of the peripheral edges of the absorbent core to form a substantially complete envelope thereabout. The barrier layer 74 can provide a covering of one or both of the major bodyside and outerside surfaces of the absorbent core 33 without being wrapped around the core. The bodyside and outerside layers of the barrier layer 74 may be composed of substantially the same material, or may be composed of different materials. For example, the outerside layer of the barrier layer 74 may be composed of a relatively lower basis weight material having a relatively high porosity, such as a wet strength cellulosic tissue composed of softwood pulp. The bodyside layer of the barrier layer 74 may have a relatively low porosity to better prevent the migration of superabsorbent particles onto the wearer's skin. In another arrangement, a spacer layer (not shown) may be interposed between the absorbent inner structure 32 and the backsheet barrier layer 30 to provide desired benefits. Where the backsheet barrier layer 30 is vapor permeable, the spacer layer can separate the backsheet barrier layer 30 away from the absorbent inner structure 32 to help to reduce a damp or cool feeling that may arise when the absorbent becomes wetted.

Referring now to FIGS. 2-4C, the web of scrim 40 is incorporated into the absorbent core 33 of the absorbent inner structure 32. In a representative illustration in FIG. 2, the web of scrim 40 comprises elongate strands which are arranged in a grid including spaced parallel strands 82 extending in a first direction, such as the machine-direction 24, and crossing strands 84 extending in a second direction, such as the cross-direction 26, defining openings 86 in the web of scrim. The shape of the openings 86 can include, but are not limited to, squares, rectangles, diamonds, or parallelograms. Among other things, the openings 86 permit liquid in the absorbent core 33 to flow substantially unhindered through the web of scrim 40. The strands 82, 84 are secured to each other where they intersect to create a lattice providing strength and stability to the absorbent core 33. The scrim position in the thickness direction 25 within the absorbent core 32 is preselected.

In use, the web of scrim 40 brings added integrity to the absorbent inner structure 32 by holding the matrix of the fibrous material together against loads applied through movement of the wearer and by liquid insults. These loads tend to cause the fibrous material (and hence the absorbent core 33) to rupture or tear apart. The web of scrim 40 resists forces applied to the absorbent core 33 such as but not limited to tensile, compressive, and shear forces. The web of scrim 40 allows the absorbent core 33 to have a lower basis weight of fibrous material because of the additional strength provided by the web of scrim. It is to be understood that the basis weight of the absorbent core 33 may be selectively varied over its surface area to customize regions where the most absorbency is required. Accordingly, the construction of a thinner absorbent core 33 and a thinner absorbent inner structure 32 is facilitated.

Conventionally, the web of scrim 40 is made of suitable material that provides desired levels of strength and flexibility. For example, the strands 82, 84 of the web of scrim 40 may be composed of natural or synthetic materials, as well as combinations thereof. Examples of suitable non-elastomeric materials are given in co-assigned application Ser. No. 10/306,086 entitled ABSORBENT ARTICLE WITH REINFORCED ABSORBENT STRUCTURE by Heyn et al., filed Nov. 27, 2002, and co-assigned European Patent Publication No. 0 467 409 A1, the disclosures of which are incorporated herein by reference.

In one embodiment of the present invention, the web of scrim 40 is made of an elastomeric or extensible material, broadly a stretchable material, to provide the desired integrity while permitting greater stretchability of the absorbent core 33 in the MD and/or CD directions. As used herein, "elastomeric" refers to a material or composite which can be elongated by at least 25 percent of its relaxed length and which will recover, upon release of the applied force, at least 10 percent of its elongation. Suitably, the elastomeric material or composite is capable of being elongated by at least 50 percent, more suitably by at least 100 percent, of its relaxed length and recover, upon release of an applied force, at least 50 percent of its elongation. "Extensible" refers to a material or composite that is stretchable or capable of being elongated in at least one direction, but which may not have sufficient recovery to be considered to be elastic. Any suitable stretchable fiber forming resins or blends containing the same may be utilized for scrim 40. For example, scrim 40 may be made from block copolymers having the general formula A-B-A' where A and A' are each a thermoplastic polymer endblock which contains a styrenic moiety such as a poly (vinyl arene) and where B is an elastomeric polymer midblock such as a conjugated diene or a lower alkene polymer. The web of scrim may be formed from, for example, (polystyrene/poly(ethylene-butylene)/polystyrene) block copolymers available from KRATON™ Polymers under the trademark KRATON G. One such block copolymer may be, for example, KRATON™ G1657M.

Other exemplary elastomeric materials which may be used to form elastomeric scrim 40 include polyurethane elastomeric materials such as, for example, those available under the trademark ESTANE from Noveon, Inc., polyamide elastomeric materials such as, for example, those available under the trademark PEBAX from the Rilsan Company, and polyester elastomeric materials such as, for example, those available under the trade designation Hytrel from E. I. DuPont De Nemours & Company. Alternative polymers for the web of scrim 40 include those referred to as single site catalyzed polymers such as "metallocene" polymers. The term "metallocene-catalyzed polymers" as used herein includes those polyolefin polymers that are produced using metallocenes or constrained geometry catalysts, a class of organometallic complexes, as catalysts. For example, a common metallocene is ferrocene, a complex of a metal between two cyclopentadienyl (Cp) ligands. Such metallocene polymers are available from ExxonMobil Chemical Company of Baytown, Tex. under the trade name EXXPOL® for polypropylene based polymers and EXACT® for polyethylene based polymers and from Dow Chemical Company of Midland, Mich. under the name ENGAGE®. Desirably, the single site catalyzed polymers are selected from copolymers of ethylene and 1-butene, copolymers of ethylene and 1-hexene, copolymers of ethylene and 1-octene and combinations thereof. Examples of suitable copolymers include the AFFININTY® series of elastomers and plastomers available in the density ranges of 0.86 g/cc to 0.96 g/cc offered by the Dow Chemical Company of Midland, Mich. Commercial elastomeric scrim is available from Conwed Plastics, Minneapolis, Minn. under the trademark REBOUND®. General characteristics include an extension of 200% or greater and high recovery rates during cycling. An example is REBOUND® 1000 which has a basis weight of 54 gsm, a rectangular mesh geometry of 5.3×4.0 strands per inch and a recovery force of 150 grams per inch width at 200% extension in the machine direction.

Still further, the web of scrim 40 could be formed of one material and coated with another material, or be a biodegradable material, such as polylactic acid. An example of a superabsorbent coating is given in co-assigned application Ser. No. 10/246,811 entitled ABSORBENT ARTICLES HAVING A SUPERABSORBENT RETENTION WEB by Newbill et al., filed Sep. 18, 2002, the disclosure of which is incorporated herein by reference.

In FIG. 1, the web of scrim 40 is shown extending the full length of the absorbent core 33, but may have a lesser or greater length. The inner absorbent core 33 has longitudinal outer side edges 87. The web of scrim 40 is narrower than the absorbent core 33 and arranged so that its longitudinal side edges 88 are located inwardly of the longitudinal edges 87. In this way, longitudinal edges 88 of the web of scrim 40 are embedded in and shielded by the fibrous material of the absorbent core 33 so they do not irritate the skin or abrade or poke holes in other parts of the diaper 10. The core 33 is shown in FIG. 1 to extend lengthwise of the diaper and to embed the web of scrim 40. It has been found that the web of scrim 40 helps the absorbent core 33 hold its shape in conformance with the wearer's body thereby maintaining integrity of fit and comfort in both wet and dry conditions.

Figure 3:
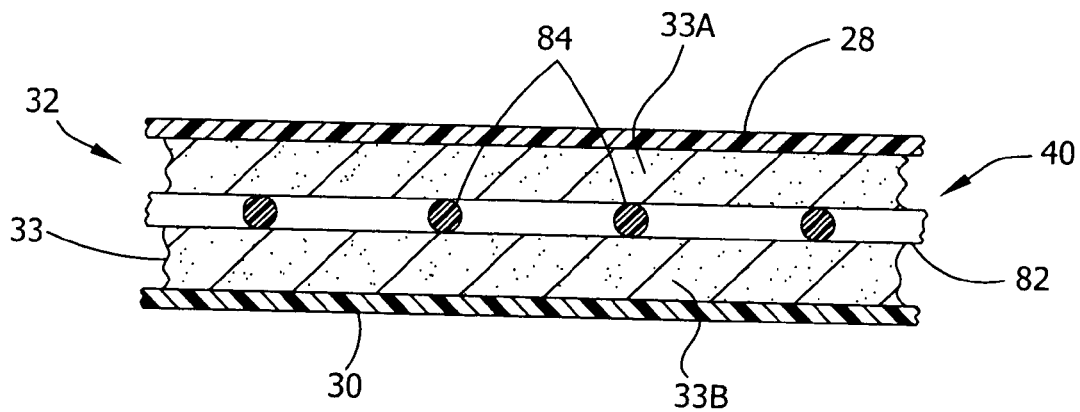
FIG. 3 is an enlarged, fragmentary cross-section of the absorbent core taken along line 3-3 of FIG. 2.

The web of scrim 40 typically defines a substantially central or intermediate position in the direction 25 between upper and lower regions 33A and 33B of the absorbent core 33 (FIG. 3). However, because the web of scrim 40 is narrower than the absorbent core 33, the upper and lower regions 33A, 33B have no dividing boundary plane and are not distinct away from the web of scrim. The web of scrim 40 may be incorporated in the absorbent core 33 in a suitable manner, such as during the formation of the absorbent core. Suitable air forming methods and apparatus for such incorporation are disclosed in co-assigned U.S. patent application Ser. No. 10/306,269, entitled PROCESS AND APPARATUS FOR MAKING A REINFORCED FIBROUS ABSORBENT MEMBER, by Venturino et al. and Ser. No. 10/305,755, entitled PROCESS AND APPARATUS FOR AIR FORMING AN ARTICLE HAVING A PLURALITY OF REINFORCED SUPERIMPOSED FIBROUS LAYERS, by Heyn et al., and Ser. No. 10/306,186, entitled CONTROLLED PLACEMENT OF A REINFORCING WEB WITHIN A FIBROUS ABSORBENT by Venturino et al., all filed Nov. 27, 2002, the disclosures of which are incorporated herein by reference. It is noted that these forming methods and apparatus promote the entanglement of the fibers with the web of scrim 40 and with each other during manufacture of the absorbent core 33. This mechanical connection between the upper region 33A and the lower region 33B, and between both of those regions and scrim 40, is discussed more fully in co-assigned U.S. patent application Ser. No. 10/306,086 (previously cited and incorporated by reference).

At least some fibers from the upper region 33A pass through openings 86 in the web of scrim 40 and are entangled with fibers from the lower region 33B and, in the same way, at least some of the fibers from the lower region 33B pass through the openings 86 in the web of scrim 40 and are entangled with fibers in the upper region 33A whereby the upper and lower regions 33A and 33B are connected to each other by fiber entanglement through the web of scrim 40. In addition, at least some fibers from the upper and lower regions 33A and 33B may be entangled with the strands 82, 84 of the web of scrim 40 itself so there is a strong mechanical joining of the upper and lower regions 33A, 33B to each other and with the web of scrim 40. The absorbent structure does not require the use of an adhesive to bond the web of scrim 40 with the fibers of the core 33, and does not require fusion of the web of scrim with the fibers to produce a robust and durable absorbent core.

Figure 9:
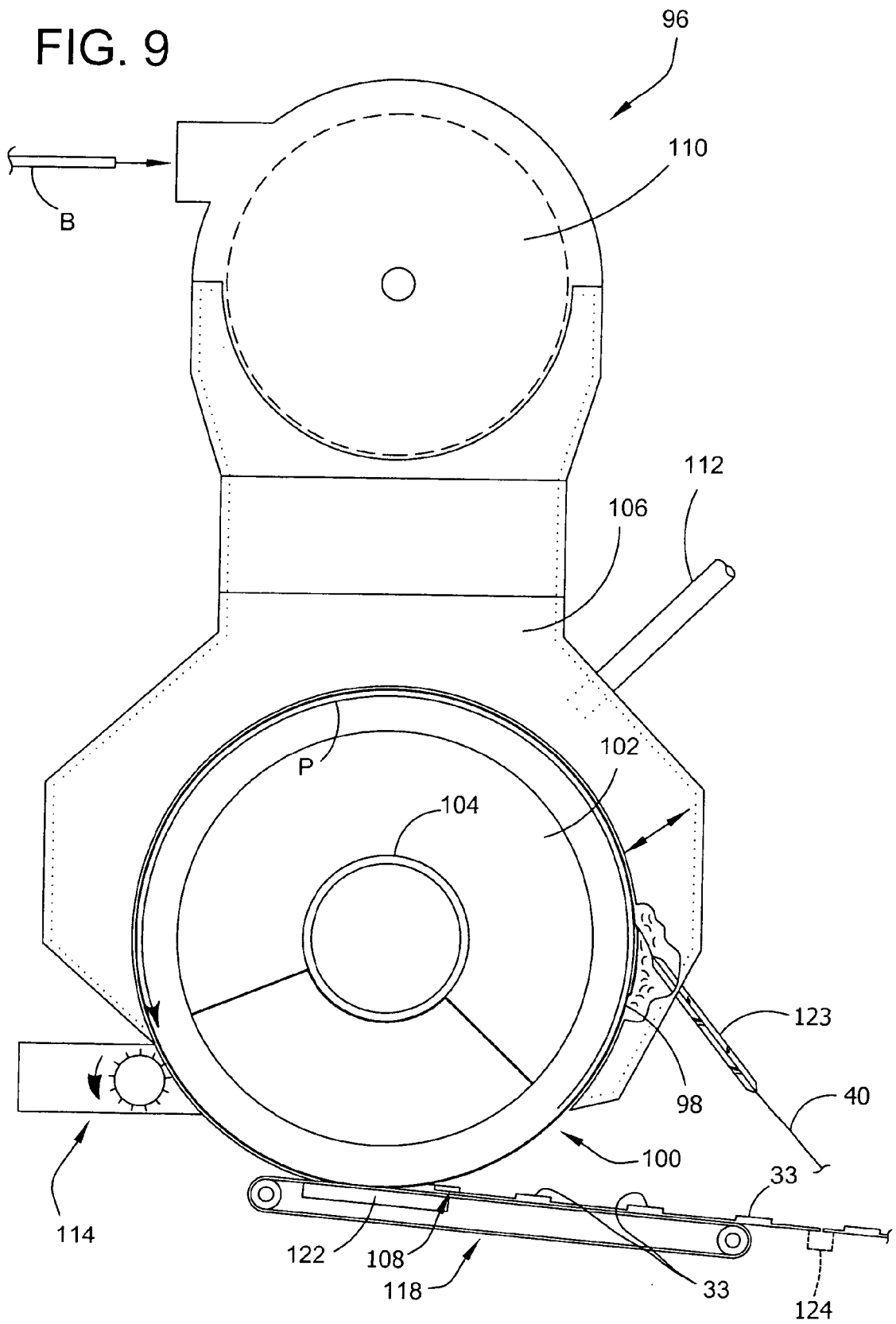
FIG. 9 is a schematic elevation of apparatus for forming an absorbent core.

Absorbent cores 33 having reinforcing members 40 may be made using conventional air forming apparatus, such as the type indicated generally at 96 in FIG. 9 and discussed more fully in the aforesaid co-pending U.S. application Ser. No. 10/306,086 (incorporated by reference). The apparatus 96 comprises a movable, foraminous forming surface 98 extending about the circumference of a rotating forming drum 100. A vacuum duct 102 is arranged to draw a vacuum under the foraminous forming surface 98. The vacuum duct 102 is mounted in fluid communication with a vacuum supply conduit 104 connected to a vacuum source (not shown).

The apparatus 96 further comprises a forming chamber 106 through which the forming surface 98 of the drum 100 is movable in a counter-clockwise direction along an arcuate path P generally from an entrance point where forming surface 98 enters the forming chamber substantially free of fibrous material past an exit point where the forming surface exits the forming chamber 106 with a continuous web 108 of absorbent material formed thereon. Absorbent cores 33 are formed by cutting the absorbent web 108 into appropriately sized article lengths.

A conventional source of fibrous material, such as a fiber supply reservoir (not shown) or a fiberizer 110 delivers a fluent fibrous material (e.g., a flow of discrete fibers) into the forming chamber 106. The fiberizer 110 shown in FIG. 9 is operatively positioned above the forming chamber 106 and can be a rotary hammer mill or a rotatable picker roll. Suitable fiberizers are available from Paper Converting Machine Company of Green Bay, Wis., U.S.A. The fibrous material may include natural fibers, synthetic fibers and combinations thereof, as previously discussed. The fibrous material employed in the apparatus 96 of FIG. 9 is derived from a batt B of wood pulp cellulose fibers fed to the fiberizer 110 which converts the batt into discrete fibers and delivers fluidized fibrous material into the forming chamber 106.

Other fibrous or particulate material for forming the absorbent web 108 may additionally be delivered into the forming chamber 106. For example, particles or fibers of superabsorbent material may be introduced into the forming chamber 106 by employing conventional mechanisms such as pipes, channels, spreaders, nozzles and the like, as well as combinations thereof. As illustrated, superabsorbent material is delivered into the forming chamber 106 by delivery conduit and nozzle system 112. The fibers, particles and other desired material may be entrained in any suitable fluid medium within the forming chamber, and any reference herein to air forming encompasses other operative techniques. The forming chamber 106 is supported by a suitable support frame (not shown). The forming surface 98 is illustrated as part of the forming drum 100, but other techniques for providing a mat or core forming surface may be employed. For example, the forming surface may be provided by an endless forming belt (not shown) of the type disclosed in U.S. Pat. No. 5,466,409 entitled FORMING BELT FOR THREE-DIMENSIONAL FORMING APPLICATIONS issued on Nov. 14, 1995.

In operation, a vacuum source draws a vacuum through the vacuum duct 102 acting on the interior of the forming surface 98, as it enters and then moves through the forming chamber 106 along a forming path P toward the exit point from the chamber. The fluidized fibrous materials and other particles within the forming chamber are drawn inwardly against the foraminous forming surface 98, and air passes inwardly through the forming surface and out of the forming drum 100 through the vacuum duct 102 and vacuum supply conduit 104. Fibers and other particulates deposited on the forming surface 98 form the absorbent web 108. Subsequently, the forming surface 98 carrying the absorbent web 108 passes out of the forming chamber 106 through the exit to a scarfing chamber 114 where the absorbent web 108 can be trimmed and shaped, and excess fibrous material is removed and transported away from the scarfing chamber 114 in a suitable manner known in the art. After the scarfing operation, the portion of the forming surface 98 on which the absorbent web 108 has been formed moves to a release zone transfer station 122 where the absorbent web is drawn away from the forming surface 98 onto a transfer station conveyor 118 or other transfer or processing equipment. The release can be assisted by the application of air pressure from the interior of the drum 100.

The apparatus 96 and method described for air forming a fibrous absorbent member is generally conventional and well known in the art. For example, see U.S. Pat. No. 4,666,647 entitled APPARATUS AND METHOD FOR FORMING A LAID FIBROUS WEB issued May 19, 1987; and U.S. Pat. No. 4,761,258 entitled CONTROLLED FORMATION OF LIGHT AND HEAVY FLUFF ZONES issued Aug. 2, 1988. Other such apparatus are described in U.S. Pat. No. 6,330,735 entitled APPARATUS AND PROCESS FOR FORMING A LAID FIBROUS WEB WITH ENHANCED BASIS WEIGHT CAPABILITY issued Dec. 18, 2001; and U.S. patent application Ser. No. 09/947,128, entitled MULTI-STAGE FORMING DRUM COMMUTATOR filed Sep. 4, 2001. Examples of techniques for introducing a selected quantity of superabsorbent particles into a forming chamber 106 are described in U.S. Pat. No. 4,927,582 entitled METHOD AND APPARATUS FOR CREATING A GRADUATED DISTRIBUTION OF GRANULE MATERIALS IN A FIBER MAT issued May 22, 1990.

Still referring to FIG. 9, the forming chamber 106 of the apparatus 96 further comprises a scrim delivery station 123 through which a reinforcing scrim member 40 is introduced into the interior of the forming chamber 106 for incorporation into the absorbent web 108. The web of scrim 40 is delivered to the forming apparatus 96 in a continuous web and at a predetermined point between the entry and exit points of the forming chamber 106 as a thickness direction control for locating the web of scrim 40 within the absorbent core 33 being formed. The web of scrim 40 is sufficiently porous to permit air flowing within the forming chamber 106 to pass through the forming surface 98 as the absorbent core is being deposited thereon, and the mesh openings 86 in the web of scrim 40 are permeable to the discrete fibers flowing within the forming chamber 106. The force of the vacuum within the forming drum 100 is believed to provide the impetus for the entanglement action of some of the fibers with the web of scrim 40.

To form discrete absorbent cores 33 embodying reinforcing scrim members 40, a cutter 124 is positioned downstream from the release zone at the transfer station 122. The cutter 124 cuts the composite web and absorbent web 108 into discrete absorbent cores 33 for further processing in making individual absorbent articles 10. The web of scrim 40 can also be cut apart upon entry into the forming chamber 106. However, by keeping the web of scrim 40 (or other reinforcing member) in a unified web during formation of the absorbent web 108 in the forming chamber 106, the web of scrim 40 is much easier to handle.

Figure 10:
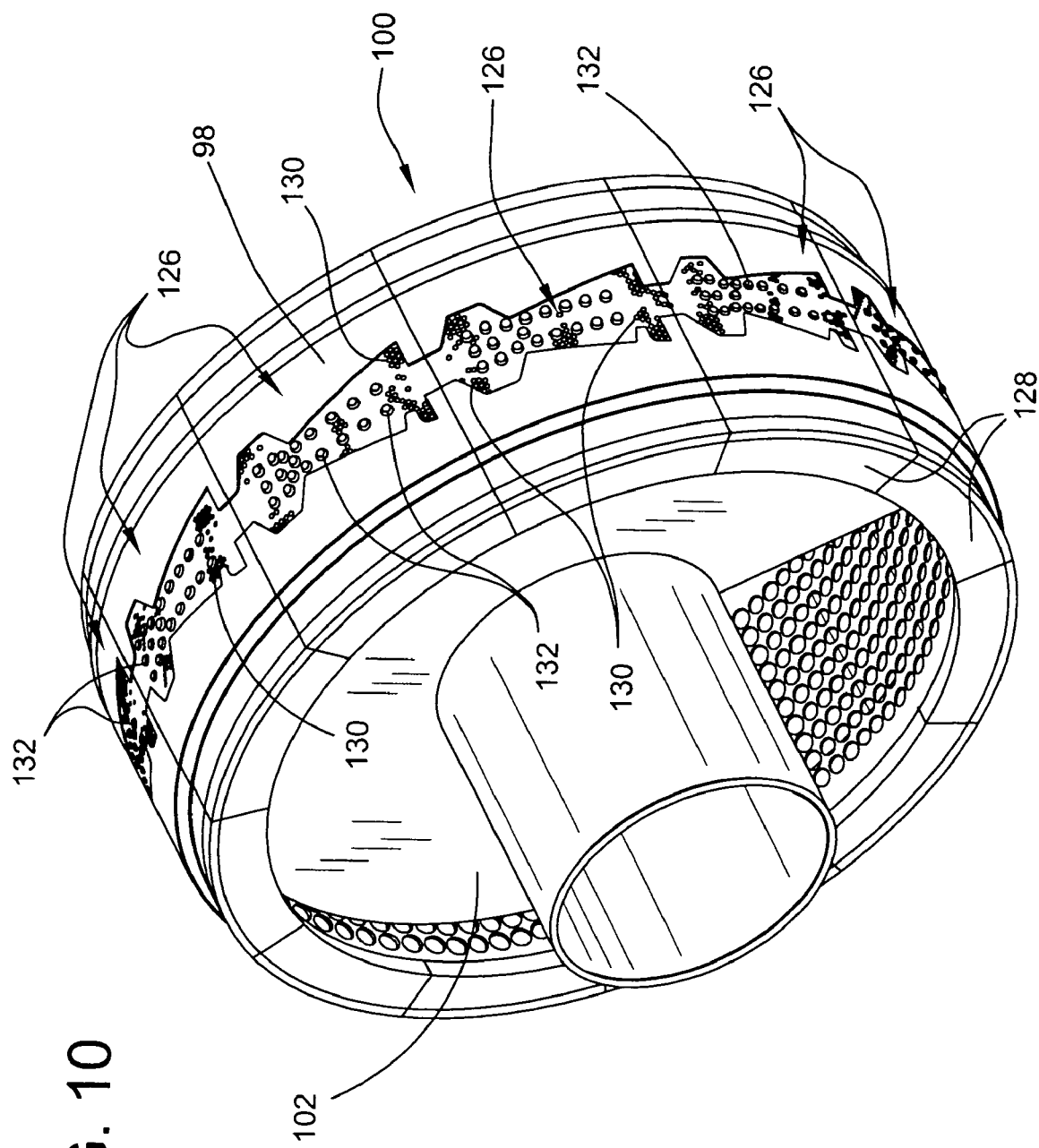
FIG. 10 is a schematic perspective of a forming drum of the apparatus of FIG. 9.

As may be seen in FIG. 10, the forming surface 98 of the drum 100 is defined by a multiplicity of forming screens (broadly, "forming members"), each designated generally at 126. The forming screens 126 are capable of independent attachment to and removal from the drum 100. However, it is to be understood that the drum 100 could have a single forming screen extending about its circumference without departing from the scope of the present invention. Each forming screen 126 includes a frame 128 mounting a screen structure 130, broadly a foraminous surface, through which air readily passes, but on which fibers (and other material) in the forming chamber are deposited to form the fibrous web. Portions of the screen structure 130 are shielded to define the peripheral shape of the absorbent core 33.

Figure 11:
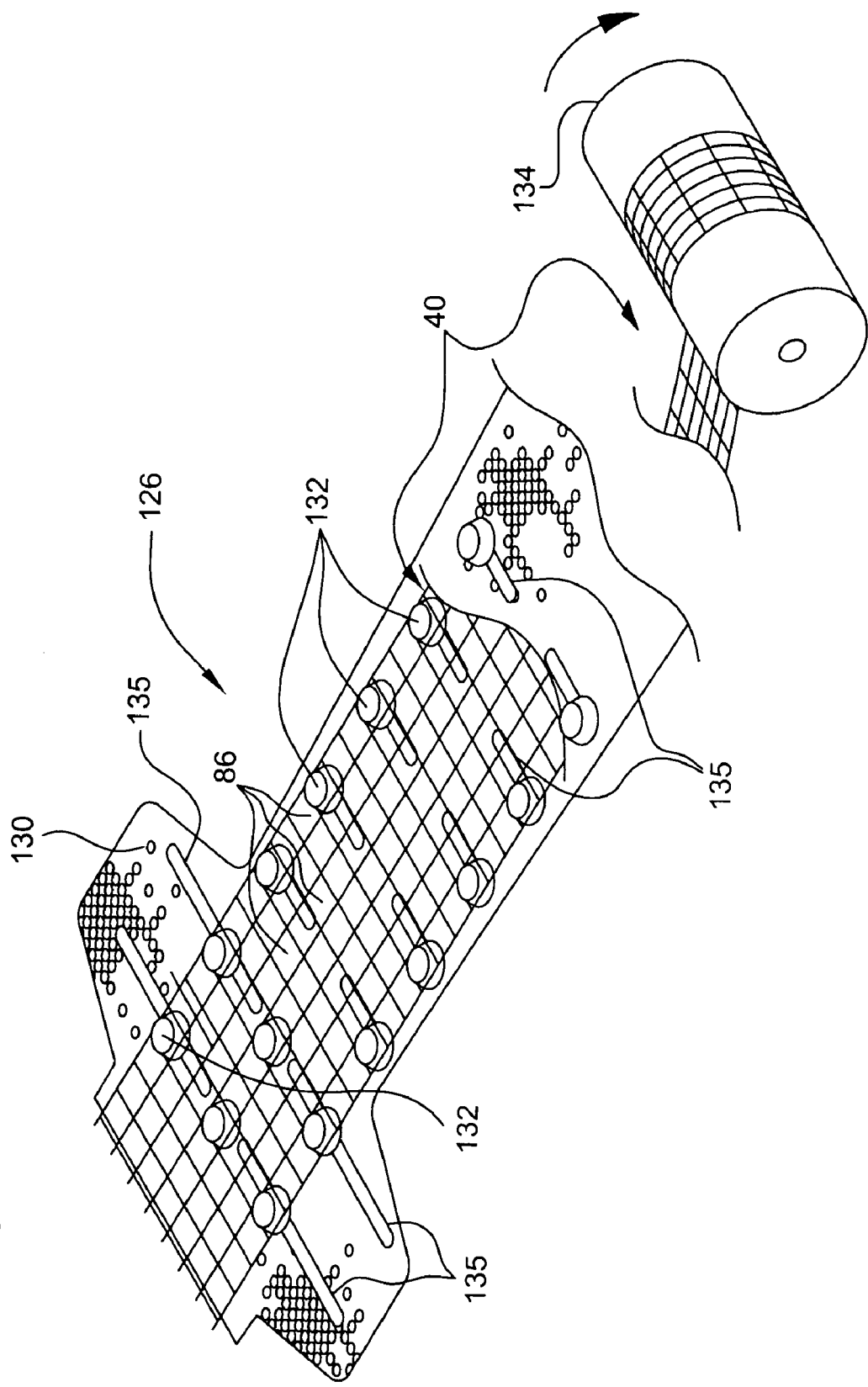
FIG. 11 is a schematic, fragmentary section of the forming screen illustrating the screen receiving the reinforcing member for forming an absorbent core of FIG. 2.

As shown in FIG. 11, the web of scrim 40 is fed from a feeding device (e.g., a roll 134 of scrim) through the scrim delivery station 123 (not shown) for feeding the web of scrim to the forming screen 126. In one embodiment, the forming screen structure 130 has multiple protrusions, such as nubs 132, slidably positioned in slots 135 projecting up from the screen structure. One skilled in the art will recognize that other protrusions, such as fingers, hooks, studs and the like may be used to hold the web of scrim 40 on the screen structure 130. In one form of operation, the web of scrim 40 is guided down in its unstretched state onto the forming screen 126 so that the nubs 132 of the screen structure 130 are received in the openings 86 of the web of scrim 40. Guiding may be accomplished using guiding equipment such as of the type described in the aforementioned co-assigned U.S. patent application Ser. No. 10/306,269. In one embodiment, the nubs 132 are used to stretch the web of scrim 40 into a stretched condition prior to the formation of the absorbent core 33 as will be more fully described below. The nubs 132 are configured to travel in the CD direction so as to stretch the web of scrim in the CD direction and suitable tension is applied to the web of scrim 40 at the scrim delivery station 123 to stretch the web of scrim in the MD direction so that the nubs hold the web of scrim in the stretched condition in both the MD and CD directions during formation of the absorbent core 33. Alternately, the web of scrim 40 is prestretched and delivered to the forming screen 126 and fastened on the nubs 132 in a stretched condition.

Figure 4C:
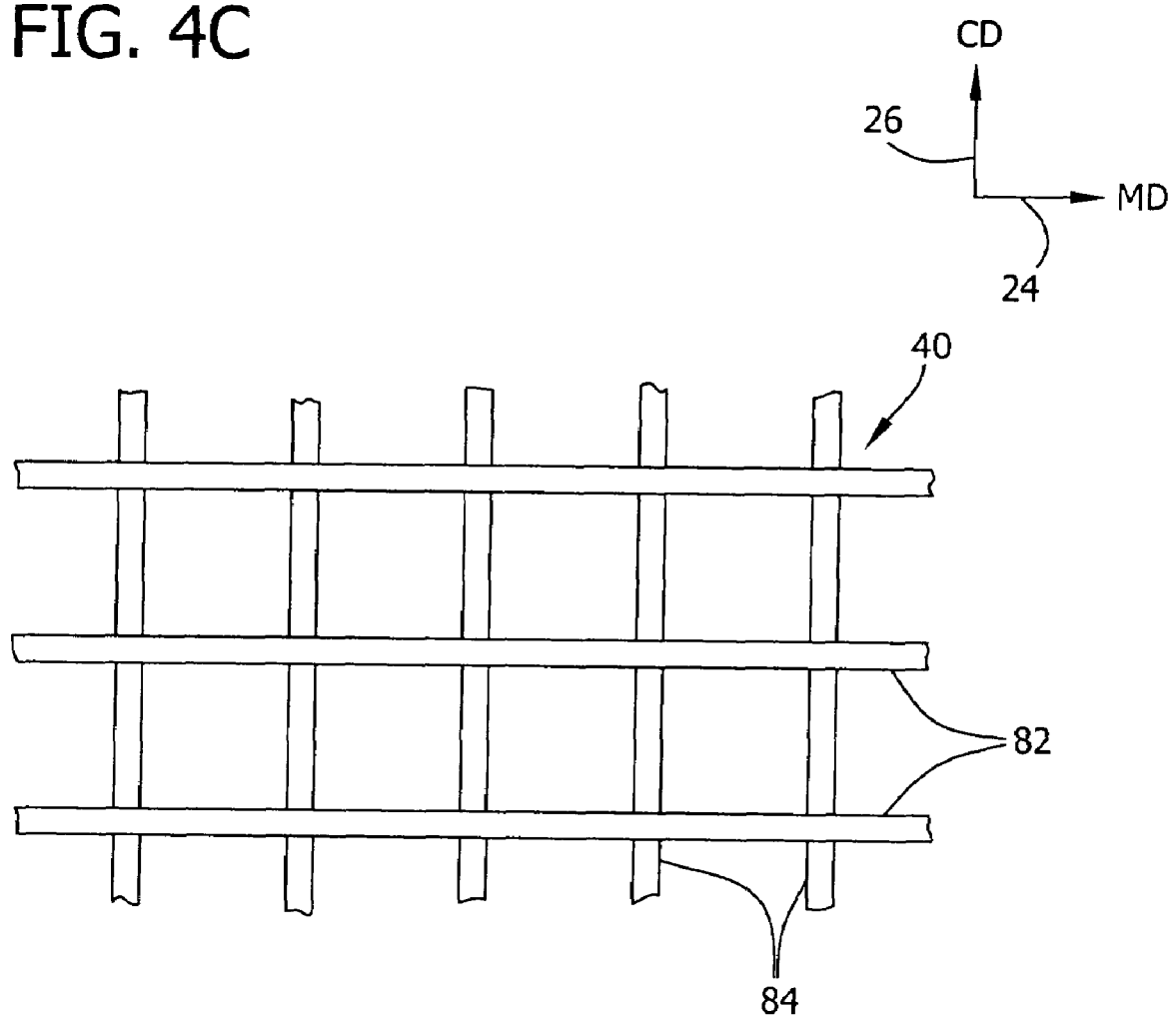
FIG. 4C is an enlarged, fragmentary plan view of a reinforcement member similar to 4A shown elongated in both the machine direction and cross direction.
Figure 5A:
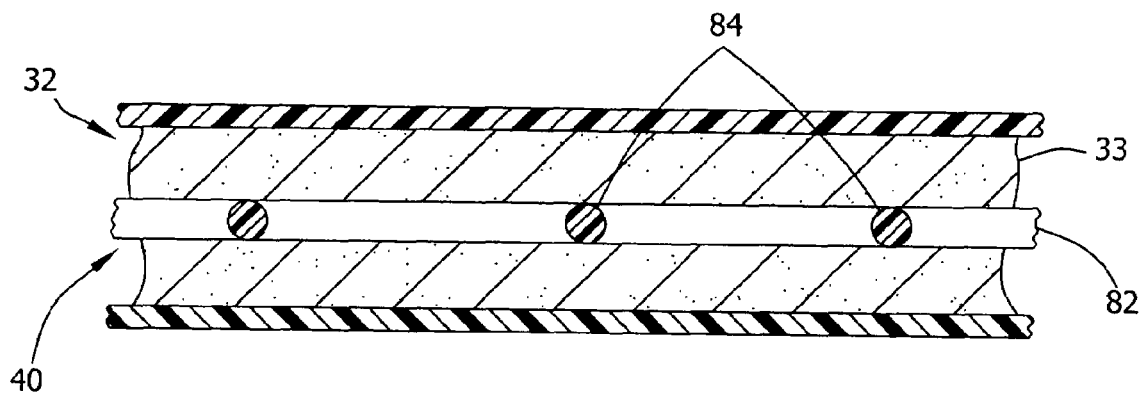
FIG. 5A is an enlarged, fragmentary cross-section of an absorbent structure with the reinforcement member and the absorbent core in a stretched condition.
Figure 5B:
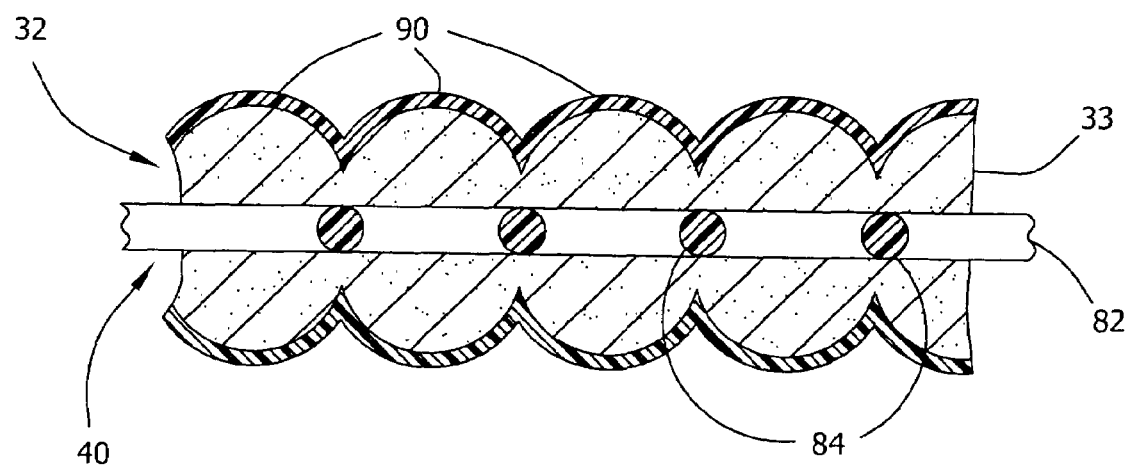
FIG. 5B is an enlarged, fragmentary cross-section of the absorbent structure of FIG. 5A in a relaxed condition showing rugosities in the absorbent core.

Referring now to FIGS. 4A-5B, in one embodiment, the absorbent material of the absorbent core 33 is entangled with the web of elastomeric scrim 40 while the web of scrim is in a stretched condition. The web of scrim 40 is stretched in the machine direction 24 as shown in FIG. 4A, cross-machine direction 26 as shown in FIG. 4B, or both directions 24, 26 as shown in FIG. 4C before the absorbent core 33 is formed on the web of scrim. The absorbent material is joined to the tensioned elastomeric scrim 40 as shown in FIG. 5A by entangling the fibers as described above so that upon release of the tensioning force on the elastomeric scrim, the web of scrim gathers the absorbent core 33 to form rugosities 90 in the absorbent material as shown in FIG. 5B. The resulting absorbent core 33 is stretchable, has increased surface area and is soft to the touch. By forming the absorbent core 33 in this way, the core is stretchable without requiring the absorbent material to be stretchable. As the core 33 stretches (e.g., under the load of multiple urine insults) the absorbent material merely flattens out reducing the height of some of the rugosities 90 as the core extends to its formation size as shown in FIG. 5A. Additionally, the resultant "pillows" created by the rugosities 90 are visually appealing. The pattern and extension of the web of scrim 40 have a role in the height and frequency of the rugosity pattern. As will be understood, elastomeric scrim with different retraction forces can be used to obtain different degrees of rugosities 90. The higher the retraction forces of the elastomeric scrim, the higher the rugosities 90 or mounds will be.

The absorbent core 33 can be formed around the web of scrim 40 while the web of scrim is suitably extended between about 25% and 300% of its relaxed dimensions, more desirably between about 50% to about 150%, and even more desirably about 100% of its relaxed dimensions. One advantage of forming the absorbent core 33 in the stretched condition is the core can be formed with a lighter basis weight because when the stretched web of scrim 40 is allowed to relax, the web of scrim pulls the absorbent core together to form a higher basis weight structure. Absorbent inner structure 32 forming speeds may be increased because lighter basis weight cores 33 allow more forming air to pass through during formation. Another advantage is that narrower absorbents, particularly in the crotch width, can be manufactured while providing the necessary surface area for efficient forming air flow rates.

The absorbent core 33 may also be zoned so that one portion of the core has a higher basis weight than another portion. Suitably techniques for forming zoned absorbent structures are disclosed in co-assigned U.S. Pat. No. 4,761,258 entitled CONTROLLED FORMATION OF LIGHT AND HEAVY FLUFF ZONES by K. Enloe which issued Aug. 2, 1988; U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001; and U.S. patent application Ser. No. 10/207,929 entitled APPARATUS AND FORM FOR MAKING AN AIR FORMED FIBROUS WEB by Venturino et al., filed Jul. 30, 2002, the disclosures of which are incorporated by reference. The absorbent core 33 is suitably formed with the web of scrim 40 in the stretched condition, and the core has a maximum formed basis weight in the range of about 100 to about 1200 grams/square meter (gsm), more desirably within the range of about 400 to about 800 gsm, and even more desirably about 600 gsm. The maximum basis weight of the final absorbent core 33 is desirably in the range of about 150 to about 1600 grams/square meter (gsm), more desirably within the range of about 600 to about 1400 gsm, and even more desirably about 1200 gsm.

In one embodiment, the upper layer 33A of the absorbent core is formed using air forming apparatus having a scrim delivery station 123 through which the reinforcing web of scrim 40 is introduced into the interior of the forming chamber 106 for incorporation into the absorbent web 108 of the type discussed in the aforesaid co-pending U.S. application Ser. No. 10/306,086. For example, an unstretched elastomeric scrim 40 for diaper 10 of size 4 designed to fit a baby weighing 22-37 lbs may suitably have a width at the narrowest point of the absorbent member in the range of about 3.0 cm to about 8.0 cm, and more desirably within the range of about 4.0 to about 7.5 cm, and a length in the range of about 30 to about 40 cm, and more desirably within the range of about 34 to about 38 cm long. The web of scrim 40 is stretched over the forming screen 126 (FIG. 11) and secured on the screen structure 130 using nubs 132 (FIG. 11). Pins, pegs or other devices and techniques may be used to secure the web of scrim to the forming screen 126 in the stretched condition. The web of scrim 40 is elongated or stretched in the width or CD direction by about 25% to about 300%, and more desirably within the range of about 50% to about 150%, and stretched in a length or MD direction by about 0 to about 300%, and more desirably within the range of about 0-100%. The second layer 33B is formed by entangling the absorbent material with the web of scrim 40 and the first layer 33A while the elastomeric scrim is maintained in the stretched condition, thus forming the absorbent core around the web of scrim in its stretched state. The absorbent core 33 may be pressed as is known in the art while the web of scrim is still in the extended state. The web of scrim 40 is then allowed to relax, causing rugosities 90 to form in the absorbent material. The resulting composite absorbent inner structure 32 has a width at the narrowest point in the range of about 4.0 to about 12.0 cm, and more desirably within the range of about 5.0 to about 10.0 cm, and a length in the range of about 30.0 to about 40.0 cm, and more desirably within the range of about 34.0 to about 38.0 cm, long. To the extent that the absorbent core 33 exhibits some resistance to being gathered, the elastomeric scrim 40 will be unable to fully recover to its unstretched dimension once it is joined to the absorbent core 33. The rugosities 90 in the absorbent core 33 allow the composite absorbent inner structure 32 to have stretch and recovery in substantially all directions along the length and width of the structure.

Without being bound by any particular theory, the recovery of elastomeric scrim 40 within an absorbent core can prevent or destroy some of the bonding formed during the densification of the absorbent core 33 or by other bonding methods known in the art (i.e., adhesives, synthetic fibers). This disruption of the absorbent core network can be directed in any direction (MD, CD, or TD). The retraction of the web of scrim 40 may break apart hydrogen or any other bonds and tear apart or detangle some of the entangled fibers within the absorbent core 33. For example, certain absorbent cores are highly compressed after formation to achieve a desired level of consolidation to allow efficient processing and packaging. However, this densification results in undesired characteristics such as increased pad stiffness and lower permeability both of which will hamper product performance in terms of comfort and absorption. In one embodiment, an absorbent core 33 containing an elastomeric scrim 40 (such as REBOUND® 1000 as previously described) is compressed with the web of scrim in its stretched condition. After the compressive forces are removed, the absorbent core 33 and scrim 40 are allowed to relax toward their uncompressed configurations in the TD direction. This causes bonds between the fibers (and other materials in the core) to be broken in the TD direction. The core is also relaxed in the MD and CD directions, causing the web of scrim 40 to retract toward its original dimensions in the MD and CD directions. Bonds between the fibers and the web of scrim 40 are broken in the MD and CD directions by this relaxation. The controlled release of energy created by stretching and compressing the absorbent core 33 and scrim 44 after the absorbent core is formed around the web of scrim imparts desired characteristics such as higher void volumes, increased flexibility and creation of textured surfaces and may be used to alter the flexibility and permeability properties of the absorbent core. The extent of disruption is dependent on the geometry, thickness, extent of extension or compression and the allowed subsequent recovery of the web of scrim. The disruption generally includes only some of the fiber network within the absorbent core and generally in the regions nearest the web of scrim 40. The resulting absorbent core will maintain the desired integrity in unaffected areas while having the additional benefits described.

Figure 6A:
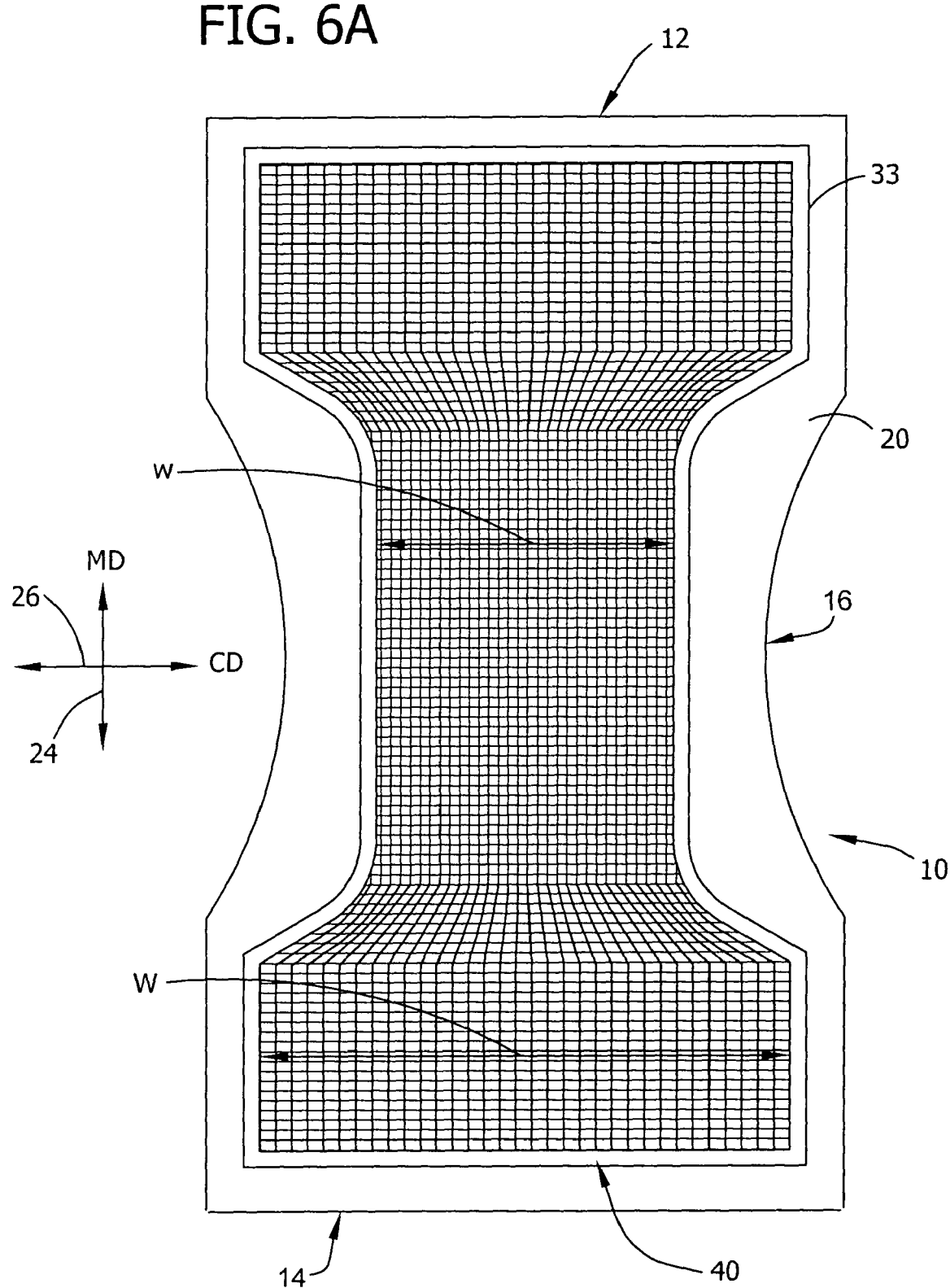
FIG. 6A is another absorbent structure including a stretched reinforcement member which generally conforms to the shape of the absorbent core.

In one embodiment, as shown in FIG. 1, the width of the web of scrim 40 is between 25% and 100%, and more preferably between 50% and 100%, of the narrowest width dimension of the absorbent core 33 (usually located at the crotch portion 16 of the core). In another embodiment of the present invention illustrated in FIG. 6A, a web of scrim 40' has a non-uniform transverse width in the CD direction 26 along the longitudinal length (i.e., in the machine direction 24) of the diaper 10. As shown in FIG. 6A, the web of scrim 40' has a first width "W" at back waistband portion 12 and front waistband portion 14 of the diaper 10 that is substantially greater than a second width "w" at the crotch portion 16 of the article such that the web of scrim has a generally hourglass shape which generally conforms to the hourglass shape of the absorbent core 33. Thus, the web of scrim 40' reinforces the wider areas of the absorbent core 33 to substantially the same extent as the narrower areas of the core.

The first width W can be wider than the second width w of the absorbent core 33 in the crotch portion 16. For example, the width W of the web of scrim 40' is suitably in the range of about 4 to about 40 cm, and more desirably within the range of about 6 to about 35 cm, although other dimensions are contemplated. The width w of the web of scrim 40' is suitably in the range of about 2.5 to about 25 cm, and more desirably within the range of about 5 to about 20 cm. For example, the ratio of the width of the wider portion of the reinforcing member to the width of the narrower portion of the reinforcing member is greater than at least about 1.5:1 and preferably greater than about 2.0:1. It is also contemplated that the web of scrim can have a wider width W in only the back waistband portion 12 or only the front waistband portion 14 of the diaper 10 such that the web of scrim is "T"-shaped without departing from the scope of this invention.

In one embodiment, the web of scrim 40' is made of a stretchable material and is selectively stretched in the back waistband portion 12 and front waistband portion 14 to the desired first width W before the absorbent fibers are entangled with the web of scrim as described above to embed the web of scrim in the absorbent core 33. The web of scrim 40' in the crotch portion 16 can be unstretched or stretched to a smaller degree of elongation than the web of scrim in the back and front waistband portions 12, 14. The web of scrim 40' can be selectively stretched and held in the extended condition during the entanglement using the movable nubs (FIG. 11) or by other suitable structure. Suitable extensible materials will maintain the desired wider width W after the force stretching the material is relieved. Additionally, the absorbent core 33 exhibits some resistance to being gathered, thus, the web of scrim 40' will be unable to fully recover to its unstretched dimension once it is joined to the absorbent core 33. The wider layer of scrim 40 in the back and front waistband portions 12 and 14 may result in improved integrity of the absorbent core 33 over a substantially greater portion of the absorbent core. Additionally, the scrim strands in the unstretched portion of scrim 40' in the crotch portion 16 will be closer together, thus allowing for more entanglement with the absorbent fibers and increasing the strength in the crotch portion.

Figure 6B:
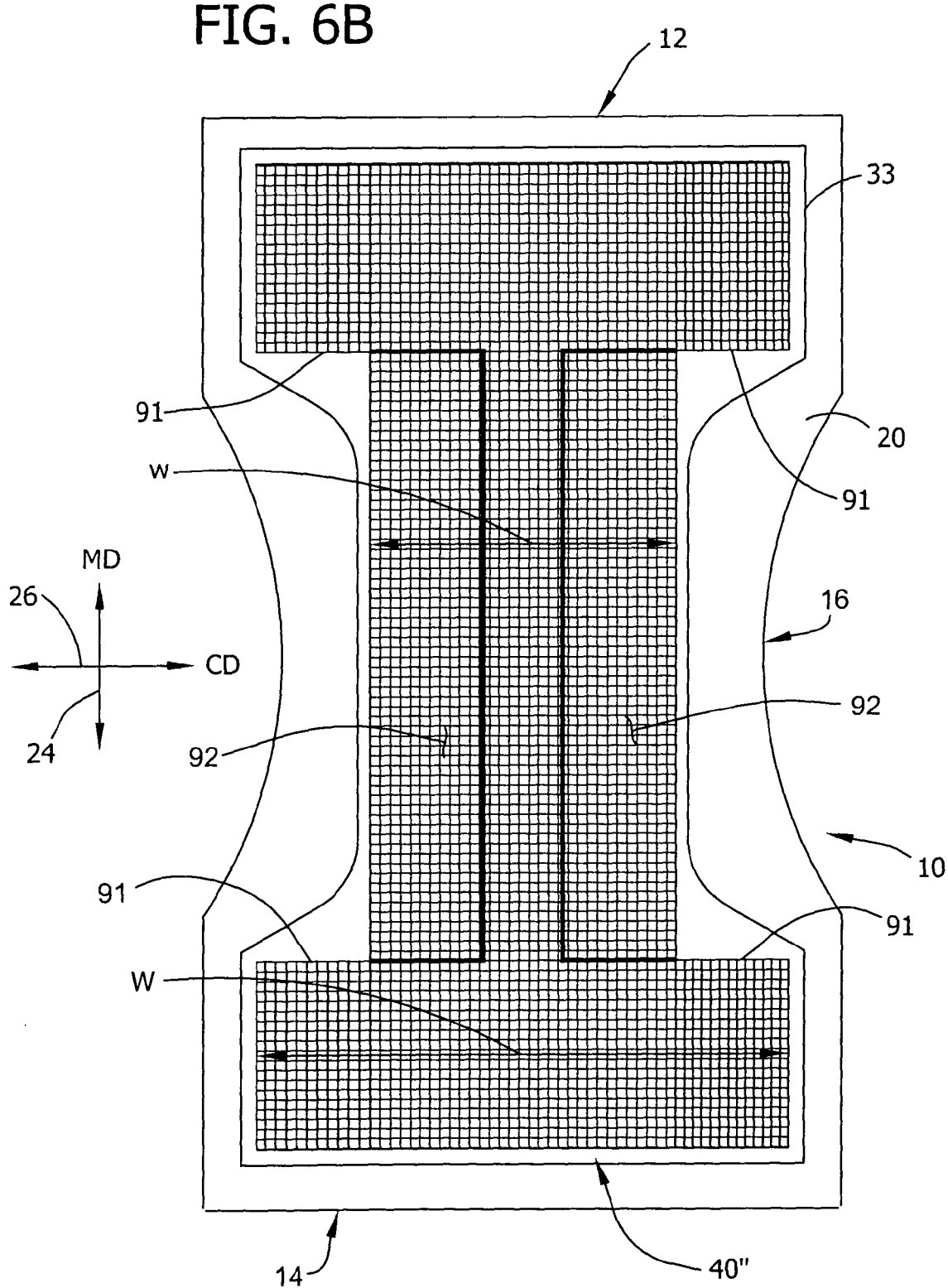
FIG. 6B is another absorbent structure including a folded reinforcement member which generally conforms to the shape of the absorbent core.

Alternately, a wide ribbon of scrim 40" is selectively cut in the crotch portion 16 while the web of scrim in the back and front waistband portions 12 and 14 incorporate the full scrim width. In one version, as shown in FIG. 6B, scrim 40" having the desired width W for the back and front waistband portions 12 and 14 is cut along transverse cut lines 91 near the crotch portion 16 to form flaps 92 in the web of scrim. The flaps 92 formed by the cuts are folded over the scrim 40" such that the web of scrim has a generally hourglass shape which generally conforms to the hourglass shape of the absorbent core 33. The folded scrim 40" has a first width "W" at back waistband portion 12 and front waistband portion 14 of the diaper 10 that is substantially greater than a second width "w" at the crotch portion 16 of the web of scrim. The web of scrim is embedded in the absorbent core 33 as described above. In a second version (not shown), the wide ribbon of the web of scrim (like scrim 40", but uncut and unfolded) having the desired width for the back and front waistband portions 12 and 14 is embedded in the absorbent core 33 and the excess scrim extending from the absorbent core in the crotch portion 16 is trimmed off before or after the web of scrim is embedded in the absorbent core 33.

Figure 7:
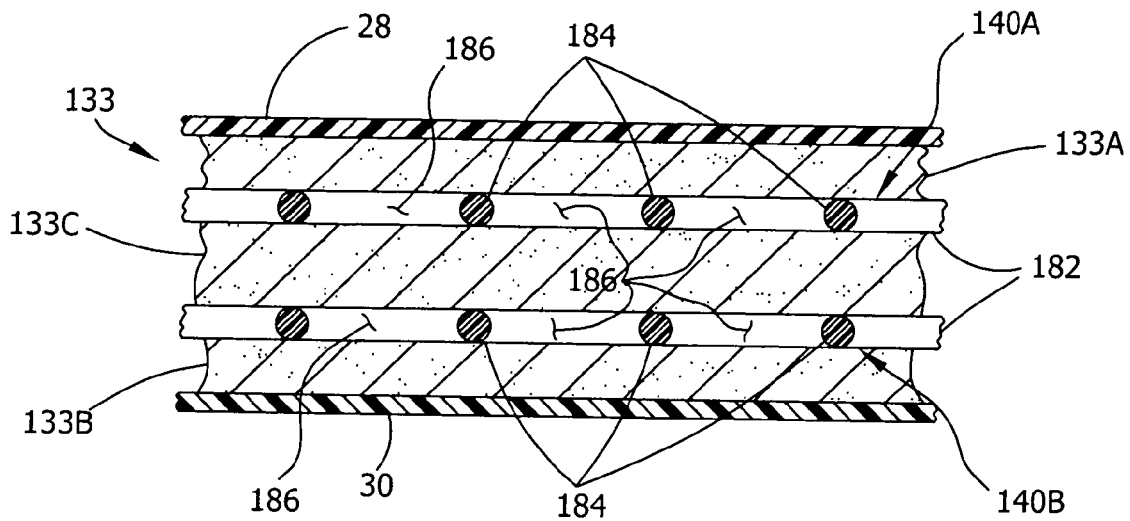
FIG. 7 is an enlarged, fragmentary cross section of an absorbent structure having two reinforcement members.
Figure 8A:
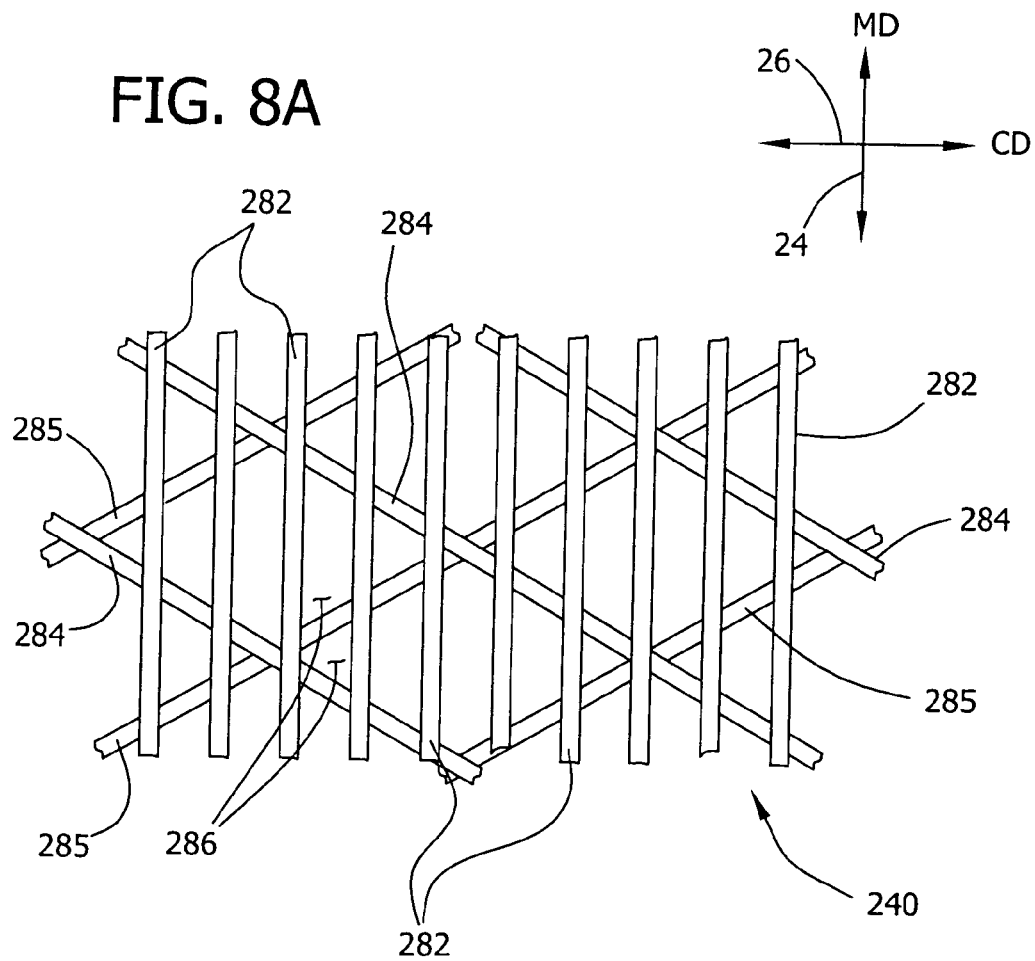
FIG. 8A is another reinforcement member embodiment having non-orthogonal crossing members.
Figure 8B:
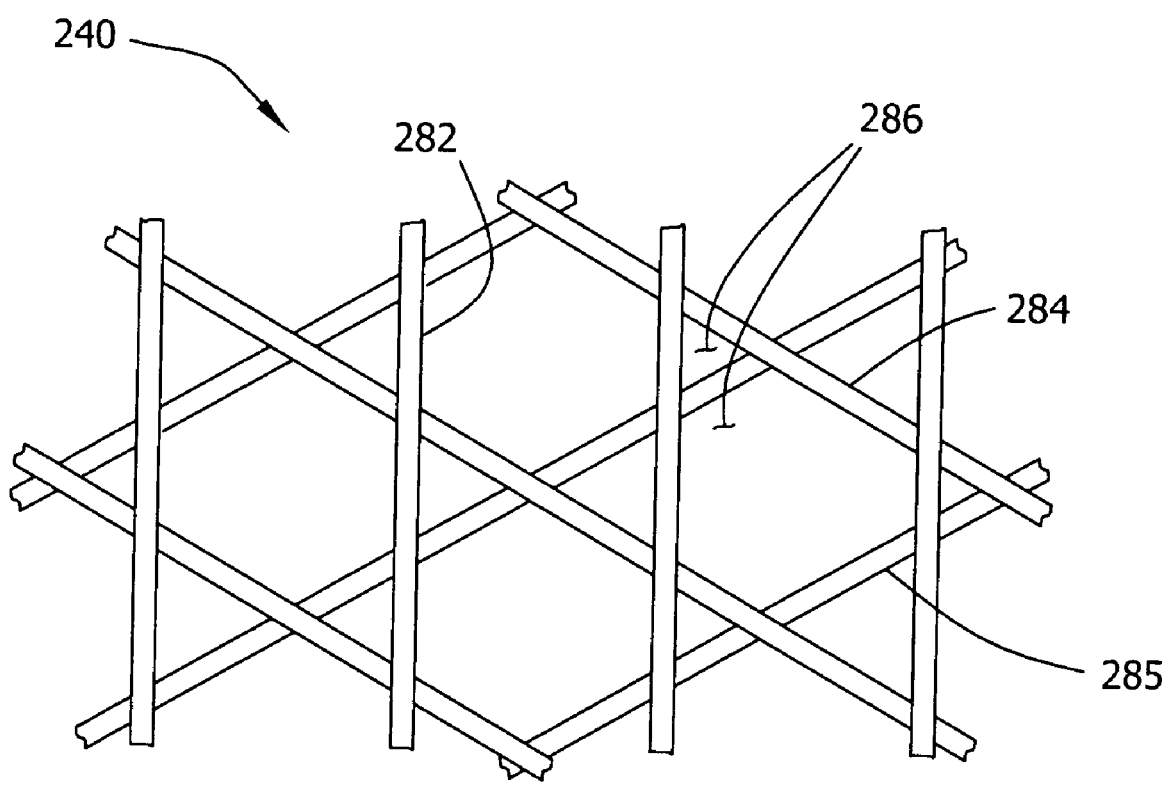
FIG. 8B is a view of the reinforcement member of FIG. 8A elongated in the cross-direction.

Referring now to FIGS. 7-8B, further embodiments of reinforcing scrim are illustrated for carrying out the present invention. Referring particularly to FIG. 7, the reinforcing member includes a first elastomeric scrim element 140A and a second elastomeric scrim element 140B arranged in layers within absorbent core 133. As shown in FIG. 7, the first element 140A is above the second element 140B. The first and second scrim elements 140A, 140B define upper, lower and middle regions 133A, 133B and 133C in absorbent core 133. However, because the scrim elements 140A, 140B are narrower than the absorbent core 133, the upper, lower and middle regions 133A, 133B, 133C have no dividing boundary plane and are not distinct away from the web of scrim. It is noted that the aforementioned forming methods and apparatus promote the entanglement of the fibers with the scrim elements 140A, 140B and with each other during manufacture of the absorbent core 133. This mechanical connection between the upper region 133A and the middle region 133C, and the middle region and the lower region 33B, and between the regions and scrim elements 140A, 140B, is as described above and discussed more fully in co-assigned U.S. patent application Ser. No. 10/306,086 (previously cited and incorporated by reference).

As shown, the scrim elements 140A, 140B have the same shape and pattern. The openings 186 of the first scrim element 140A can be aligned with the openings 186 in the second scrim element 140B. Alternately, the scrim elements 140A, 140B can be offset so that strands 182, 184 in the second scrim element are partially in registration with openings 186 in the first scrim element. Additionally, the scrim elements 140A, 140B can have different shapes or patterns without departing from the scope of the present invention. It is not necessary that the scrim elements overlie one another, or that they extend continuously over the length of the absorbent core 133. Additionally, more than two scrim elements could be used. The use of two (or more) elements 140A, 140B allows more reinforcing material to be put into the core 133 inexpensively and without requiring a more complex structure of the reinforcing material. Still further, the two elements (or their component parts) could be made of different materials. In use, the dual scrim elements 140A, 140B bring added integrity to the absorbent core 133 by holding the matrix of the fibrous material together against loads applied through movement of the wearer and by body exudates. There is a greater degree of reinforcement through the thickness of the absorbent core 33. As the absorbent core 133 is stretched, ruptures or tears form in the absorbent core as the fibers separate. Without being limited to a single reason, having the two scrim elements 140A, 140B may cause the absorbent core 133 to remain serviceable over a greater range of stresses and forces. As forces extend the absorbent core, tears begin to form. However, the tears will often begin to form in only one or two of the regions 133A, 133B, 133C. Thus, the initial tears will not form ruptures completely through the absorbent core 133. Having an additional layer of scrim and additional region increases the performance of the absorbent core 133.

Referring to FIGS. 8A and 8B, in another embodiment of the invention a web of scrim 240 comprises elongate strands arranged in a grid including spaced parallel strands 282 extending in the machine-direction 24 and first crossing strands 284 extending in a non-orthogonal direction with respect to strands 282 and second crossing strands 285 also extending in a non-orthogonal direction with respect to strands 282. In one embodiment, first and second crossing strands 284, 285 are arranged in an evenly spaced, crossing relationship. In this embodiment the strands 284 and 285 are shown arranged to extend from the strands 282 at diverging angles from each other. Alternately, the web of scrim 240 can have strands extending in the cross-direction and crossing strands extending therefrom in non-orthogonal directions. The strands 282, 284 and 285 define openings 286 in the web of scrim. The strands 282, 284 and 285 are secured to each other where they intersect to create a lattice providing strength and stability to absorbent core 233 (not shown). This provides a suitable strength of the web of scrim 240 in the machine-direction 24 while permitting greater ability to stretch in the cross-direction 26.

The web of scrim 240 is made of suitable elastomeric, extensible or non-elastic materials to provide a desired strength of the scrim while permitting greater stretchability in the cross-direction 26. The web of scrim 240 has increased stretchability in the cross-direction 26 due to the absence of strands extending in the cross-direction even if made from a non-elastomeric material. FIG. 8B illustrates the web of scrim 240 in a stretched condition with cross direction elongation of openings 286.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent structure comprising an absorbent member at least partially made of fibers and a reinforcing member at least partially embedded in the absorbent member for maintaining the structural integrity of the absorbent member, the absorbent member having a first axis extending generally lengthwise of the absorbent member and a second axis perpendicular to said first axis extending generally widthwise of the absorbent member, the reinforcing member comprising a first set of substantially parallel strands, and a second set of strands that cross said first set of strands at junctions in a non-orthogonal relationship to define openings in the reinforcing member, at least some of the fibers of the absorbent member extending through the openings in the reinforcing member and being entangled with other fibers of the absorbent member.

2. An absorbent structure as set forth in claim 1 wherein the second strands are generally parallel to each other.

3. An absorbent structure as set forth in claim 1 wherein the first set of strands extends generally parallel to one of said first and second axes.

4. An absorbent structure as set forth in claim 1 wherein the first set of strands extend generally parallel to the first axis of the absorbent member so that the reinforcing member is stretchable along at least said second axis of said absorbent structure.

5. An absorbent structure as set forth in claim 1 wherein the strands are joined to each other at least at some of the junctions.

6. An absorbent structure as set forth in claim 1 wherein said reinforcing members comprise a third set of strands that cross said first set of strands in a non-orthogonal orientation and also cross said second set of strands.

7. An absorbent structure as set forth in claim 6 wherein the strands in the second set of strands are joined to strands in the third set of strands at least at some junctions where the sets cross.

8. An absorbent structure as set forth in claim 6 wherein the strands of the second set are arranged generally perpendicular to the strands of the third set.

9. An absorbent structure as set forth in claim 1 wherein the reinforcing member is made from a material which is not substantially stretchable.

10. An absorbent structure as set forth in claim 1 wherein the reinforcing member is made from an elastic material.

11. An absorbent structure as set forth in claim 1 further comprising a second reinforcing member at least partially embedded in the absorbent member.

12. An absorbent structure as set forth in claim 1 in combination with an absorbent garment comprising an topsheet layer arranged for engagement with the body of a wearer, and a liquid impermeable backsheet, the absorbent structure being generally disposed between the topsheet layer and backsheet.

13. An absorbent structure comprising an absorbent member at least partially made of fibers and a reinforcing member at least partially embedded in the absorbent member for maintaining the structural integrity of the absorbent member, the reinforcing member being connected to the absorbent member and at least partially gathering the absorbent member to form rugosities on a surface of the absorbent member.

14. An absorbent structure as set forth in claim 13 wherein the reinforcing member is elastically stretchable.

15. An absorbent structure as set forth in claim 14 wherein the reinforcing member is relaxed from a stretched condition in which connection of the reinforcing member to the absorbent member is made.

16. An absorbent structure as set forth in claim 13 wherein the absorbent member is gathered along a first axis extending generally lengthwise of the absorbent member and along a second axis extending generally widthwise of the absorbent member.

17. An absorbent structure as set forth in claim 13 wherein the basis weight of the absorbent member when the absorbent structure is stretched to remove gathering of the absorbent member is less than about 1200 grams per square meter.

18. An absorbent structure as set forth in claim 13 wherein the basis weight of the absorbent member when the absorbent structure is relaxed to gather the absorbent member is less than about 1600 grams per square meter.

19. An absorbent structure as set forth in claim 13 wherein the reinforcing member is adapted to return substantially to an original dimension for elongation of the absorbent structure in a direction up to about 300% of its relaxed length.

20. An absorbent structure as set forth in claim 13 wherein the reinforcing member comprises strands arranged to cross over one another at junctions to define openings in the web, the strands being joined to each other at least at some of the junctions.

21. An absorbent structure as set forth in claim 20 wherein the strands are arranged so that said openings are diamond shaped.

22. An absorbent structure as set forth in claim 13 further comprising a second reinforcing member at least partially embedded in the absorbent member.

23. An absorbent structure as set forth in claim 13 in combination with an absorbent garment comprising a topsheet layer arranged for engagement with the body of a wearer, and a liquid impermeable backsheet layer, the absorbent structure being disposed between the topsheet layer and backsheet layer.

24. An absorbent structure as set forth in claim 13 wherein the reinforcing member is elastically stretchable, and wherein the structure further comprises broken connections between the fibers and reinforcing member in at least one of a machine direction, a cross direction and a thickness direction caused by contraction of the reinforcing member within the structure.

25. An absorbent structure for absorbing liquid, the absorbent structure comprising an absorbent member at least partially made of fibers and a reinforcing member at least partially embedded in the absorbent member for maintaining the structural integrity of the absorbent member, the reinforcing member having a non-uniform transverse width, the reinforcing member having openings therein, at least some of the fibers of the absorbent member extending through the openings in the reinforcing member and being entangled with other fibers of the absorbent member.

26. An absorbent structure as set forth in claim 25 wherein the reinforcing member has a peripheral shape generally conforming to a peripheral shape of the absorbent member.

27. An absorbent structure as set forth in claim 25 wherein the reinforcing member has a first wider portion embedded in a first wider portion of the absorbent member, the first portion of the reinforcing member having a transverse width greater than a transverse width of a second narrower portion of said reinforcing member and embedded in a second narrower portion of said absorbent member.

28. An absorbent structure as set forth in claim 27 wherein the reinforcing member is stretched in said first wider portion.

29. An absorbent structure as set forth in claim 28 wherein the reinforcing member is unstretched in said second narrower portion.

30. An absorbent structure as set forth in claim 28 wherein the reinforcing member is plastically deformed by stretching in said first wider portion.

31. An absorbent structure as set forth in claim 27 wherein said second narrower portion comprises a first reinforcing member section and a second reinforcing member section folded against said first reinforcing member section to form said second narrower portion.

32. An absorbent structure as set forth in claim 27 wherein the ratio of the width of said first wider portion of the reinforcing member to the width of said second narrower portion of the reinforcing member is greater than 1.5:1.

33. An absorbent structure as set forth in claim 27 wherein the ratio of the width of said first wider portion of the reinforcing member to the width of said second narrower portion of the reinforcing member is greater than 2:1.

34. An absorbent structure as set forth in claim 25 wherein reinforcing member comprise strands arranged in a pattern in which at least some of the strands intersect one another at junctions to define openings in the reinforcing members.

35. An absorbent structure as set forth in claim 25 wherein the reinforcing member has a shape selected from the group consisting of a generally hourglass shape and a generally T-shape.

36. An absorbent structure as set forth in claim 25 wherein the reinforcing member is relaxed from a stretched condition in which connection of the reinforcing member to the absorbent member is made.

37. An absorbent structure as set forth in claim 25 further comprising a second reinforcing member at least partially embedded in the absorbent member.

38. An absorbent structure as set forth in claim 25 in combination with an absorbent garment comprising a topsheet layer arranged for engagement with the body of a wearer, and a liquid impermeable backsheet layer, the absorbent structure being disposed between the topsheet layer and backsheet layer.

39. An absorbent structure as set forth in claim 38 wherein the absorbent garment includes a crotch region adapted to fit a crotch of the wearer and a waist region adapted to fit at least a portion of a waist of the wearer, the reinforcing member being narrower in the crotch region than in the waist region.

40. An absorbent structure as set forth in claim 13 wherein the reinforcing member has openings therein, at least some of the fibers of the absorbent member extending through the openings in the reinforcing member and being entangled with other fibers of the absorbent member.

* * * * *

UNITED STATES PATENT AND TRADEMARK OFFICE
CERTIFICATE OF CORRECTION

PATENT NO.       : 7,594,906 B2  
APPLICATION NO.  : 10/620142  
DATED            : September 29, 2009  
INVENTOR(S)      : Bean et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1327 days.

Signed and Sealed this

Twenty-eighth Day of September, 2010

David J. Kappos  
*Director of the United States Patent and Trademark Office*